Figure 1:
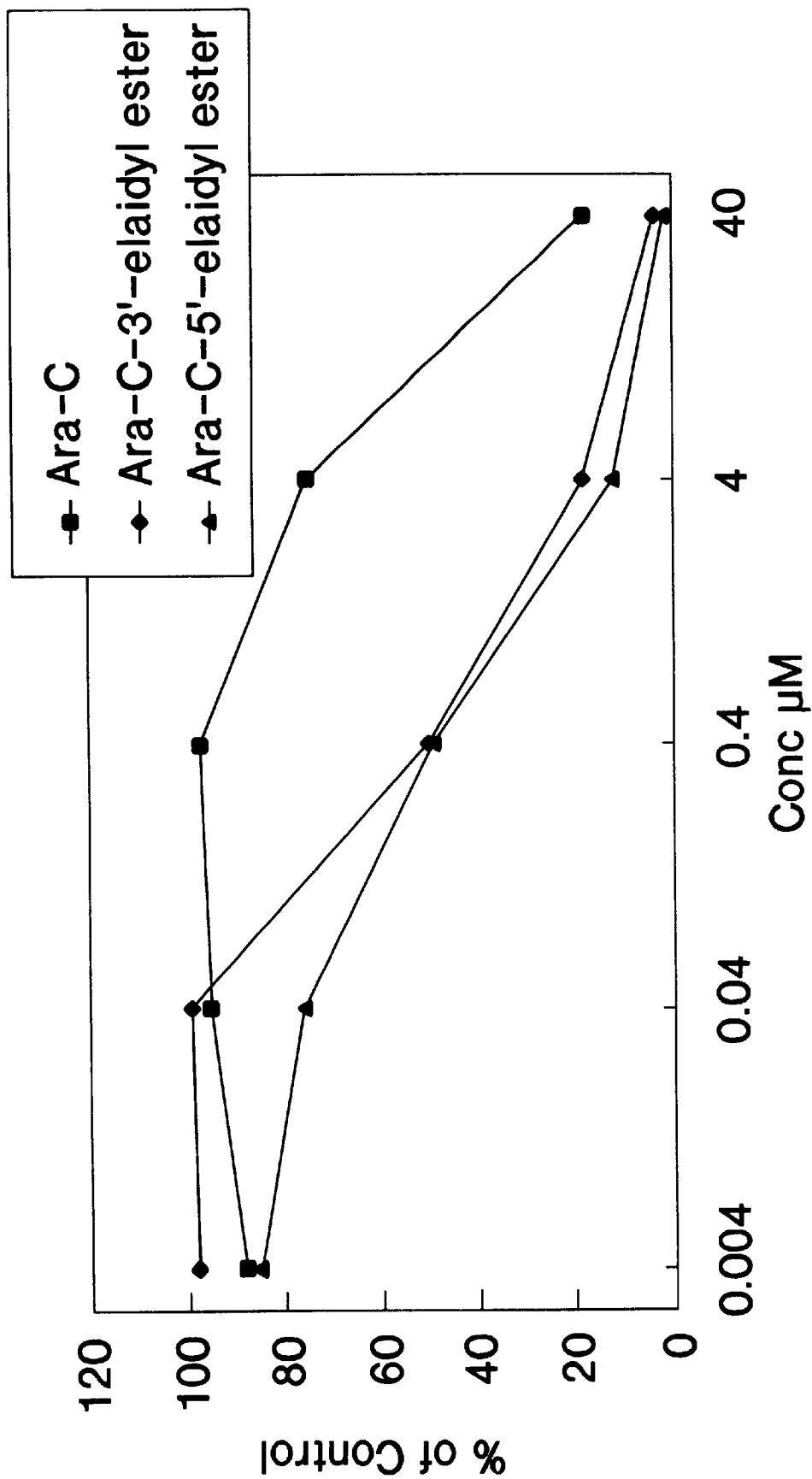

United States Patent
Myhren et al.

(12) United States Patent
(10) Patent No.: US 6,335,322 B1
(45) Date of Patent: Jan. 1, 2002

(54) THERAPEUTIC AGENTS

(75) Inventors: Finn Myhren, Porsgrunn; Bernt Børretzen, Heistad; Are Dalen, Trondheim; Kjell Torgeir Stokke, Oslo, all of (NO)

(73) Assignee: Norsk Hydro ASA, Oslo (NO)

( * ) Notice: Subject to any disclaimer, the term of this patent is extended or adjusted under 35 U.S.C. 154(b) by 0 days.

(21) Appl. No.: 09/435,641

(22) Filed: Nov. 9, 1999

Related U.S. Application Data

(60) Division of application No. 08/983,483, filed on May 26, 1998, and a continuation-in-part of application No. 08/532,754, filed on Apr. 5, 1994, now Pat. No. 6,153,594.

(30) Foreign Application Priority Data

May 4, 1993 (GB) .............................................. 9307043
Jul. 25, 1995 (GB) .............................................. 9515279

(51) Int. Cl.$^7$ .......................... A61K 31/70; C07H 19/19
(52) U.S. Cl. .............................. 514/49; 514/49; 514/50; 536/27.4; 536/28.5
(58) Field of Search ............................ 514/49, 50, 51; 536/28.5, 27.4

(56) References Cited

U.S. PATENT DOCUMENTS 5,691,319 A * 11/1997 Kaneko et al. ................ 514/49
6,153,594 A * 11/2000 Børretzen et al. ............ 514/43

FOREIGN PATENT DOCUMENTS

WO WO 94/22887 10/1994

OTHER PUBLICATIONS

R.L. Merriman, et al., "Comparison of the Antitumor activity of Gemcitabine and Ara–C in a Panel of Human Breast, Colon, Ling and Pancreatic Xenograft Models", Investigational New Drugs, vol. 14, (1996) pp. 243–247.

W. Plnkett, et al., "Preclinical Characteristic of Gemcitabine", Anti–Cancer Drugs, vol. 6, Suppl. 6, (1995) pp. 7–13.

R. A. Schwendener, Liposomen als Träger vol lipophilen Cytosinarabinosid–und Fluorodeoxyuridin–Derivaten, Onkologie, vol. 10 (Apr. 1987) pp. 232–239 (English Abstract).

R. Ohno, et al., "Treatment of Leukemia and Myelodysplastic Syndromes with Orally Administered N$^4$–palmitoyl–1–β–D–arabimofuranosylcytosine", Cancer Chemother. Pharmacol., vol. 17, (1986) pp. 161–164.

W. Rubas, et al., "Treatment of Murine L1210 Lymphoid Leukemia and Melanoma B16 with Lipophilic Cytosine Arabinoside Prodrugs Incorporated Into Unilamellar Liposomes", Int. J. Cancer, vol. 37, (1986) pp. 149–154.

R.A. Schwendener, et al., "Liposomes as Carries for Lipophilic Antitumor Prodrugs. Incorporation Characteristics and In Vivo Cytotoxic Activity", Liposomes Drug Carries, Symp. (1986) Meeting Date 1984, pp. 170–181 (Abstract Only).

Stedman's Medical Dictionary, 24th Edition, (1982) p. 817 (Baltimore, Md.).

N. Kemeny, et al., "Phase II Study of 2,2'–Anhydro–1–β–D–arabinofuranosyl–5–fluorocytosine in Advanced Colorectal Carcinoma", Cancer Treatment Reports, vol. 62, No. 3, (1978).

G.P. Bodey, et al., "Clinical Studies of β–Thioguanine Deoxyriboside Alone and in Combination with Arabinosyl Cytosine", Medical and Pediatric Oncology, vol. 2, (1976) pp. 199–205.

E.K. Hamamura, et al., "Reactions of 2–Acyloxyisobutyryl Halides with Nucleosides. 8. Synthesis and Biological Evaluation of Some 3'–Acyl and 3', 5'–Diacyl Derivatives of 1–β–D–Arabinofuranosylcytosine", Journal of Medicinal Chemistry, vol. 19, No. 5, (1976) pp. 667–674.

J.G. Moffatt, et al., Synthesis and Biologic Examination of Some Derivatives of 2,2'–Anhydro–1–(β–D–arabinofuranosyl)cytosine Hydrochloride (NSC–145668), Cancer Chemotherapy Reports, Part 1, vol. 58, No. 4, (Jul./Aug. 1974) pp. 451–469.

G.D. Gray, et al., "ImmunoSuppressive, Antiviral and Antitumor Activites of Cytarabine Derivatives", Biochemical Pharmacology, vol. 21, pp. 465–475, Pergamon Press, 1972.

D.T. Warner, et al., 'Nucleic Acids. 13.3'–O–and 2'–O–Esters of 1–β–D–Arabinofuranosylctosine as Antileukemic and Immunosuppressive Agents, Journal of Medicinal Chemistry, vol. 15, No. 8, (1972) pp. 790–792.

* cited by examiner

Primary Examiner—James O. Wilson
(74) Attorney, Agent, or Firm—Fitzpatrick, Cella, Harper & Scinto

(57) ABSTRACT

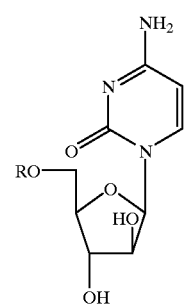

(I)

wherein R is selected from the group consisting of elaidoyl, cis-eicosenoyl and trans-eicosenoyl; and pharmaceutical compositions comprising the Ara-C derivative.

10 Claims, 21 Drawing Sheets

THERAPEUTIC AGENTS

This Application is both (a) a divisional of U.S. patent application Ser. No. 08/983,483, which was PCT filed on May 28, 1998, and (b) a Continuation-In-Part of U.S. patent application Ser. No. 08/532,754, which was PCT filed on Apr. 5, 1994, and which issued as U.S. Pat. No. 6,153,594 on Nov. 28, 2000.

This invention relates to certain nucleoside derivatives which have been found to have valuable properties for the treatment of tumours.

The nucleoside derivatives are esters of 1-β-D-arabinofuranosylcytosine (Ara-C) of formula A:

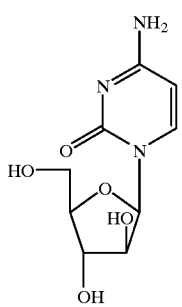

(A)

Ara-C is also sometimes known as cytosar.

Ara-C has long been known as a chemotherapeutic agent in the treatment of acute myelogenous leukaemia but has limited efficiency against solid tumours (Fre et al., Cancer Res. 29 (1969), 1325–1332; Davis et al., Oncology, 29 (1974), 190–200; Cullinan et al., Cancer Treat. Rep. 61 (1977), 1725–1726). However, even in the treatment of leukaemia Ara-C has found only limited use due to its very short biological half-life and its high toxicity.

With a view to overcoming these difficulties, a number of workers have prepared and tested pro-drug derivatives of Ara-C. For example, Hamamura et al. investigated 3'-acyl and 3',5'-diacyl derivatives of Ara-C (J. Med. Chem. 19 (1976) No. 5, 667–674). These workers prepared and tested numerous Ara-C derivatives with saturated or unsaturated ester groups containing from 2 to 22 carbon atoms, and they found that many of the compounds showed a higher activity against L1210 Leukaemia in mice than the parent nucleoside alone.

The work by Hamamura et al., and others, on pro-drug analogues of Ara-C was reviewed by Hadfield et al. in Advances in Pharmacology and Chemotherapy, 20, 1984, pages 21–67. In discussing 5'-esters of Ara-C, these authors conclude (page 27):

" . . . though many of these agents appear to function as very efficient depot forms of ara-C in mice, the analogous action in man has not been demonstrated.".

Although work has continued on pro-drugs based on Ara-C, including 3'- and 5'-acyl derivatives (see, for instance, Rubas et al. in Int. J. Cancer, 37, 1986, pages 149–154 who tested liposomal formulations of, inter alia, 5'-oleyl-Ara-C against L1210 Leukaemia and Melanoma B16) to date no such drugs have become available to the clinician.

The mode of action of Ara-C relies on its enzymatic recognition as a 2'-deoxy-riboside and subsequent phosphorylation to a nucleoside triphosphate which competes with the normal CTP for incorporation into DNA. The 2'-hydroxyl group causes steric hindrance to rotation of the pyrimidine base around the nucleosidic bond. The bases of polyarabinonucleotides cannot stack normally, as do the bases of polydeoxynucleotides. Ara-C inhibits DNA repair and DNA synthesis both by slowing down chain elongation and movement of newly replicated DNA through the matrix-bound replication apparatus. The mechanism of action of Ara-C results in an "unbalanced growth" in dividing cells. Ara-C acts in the S-phase of the cell cycle. For continuos inhibition of the DNA synthesis and finally cell death, it is crucial that Ara-C is a present at a sufficiently high concentration during at least one cell cycle.

A main reason why Ara-C is not used in the treatment of solid tumours is again the rapid clearance of the active drug from cancer cells and plasma. It is apparently not possible to achieve significant intracellular levels of drug in the neoplastic tissue, even though the tumour in question is sensitive to Ara-C in-vitro. The surprisingly prolonged half life and altered tissue distribution. of the products of this invention will be of great importance for the therapeutic effect of these products.

Figure 7:
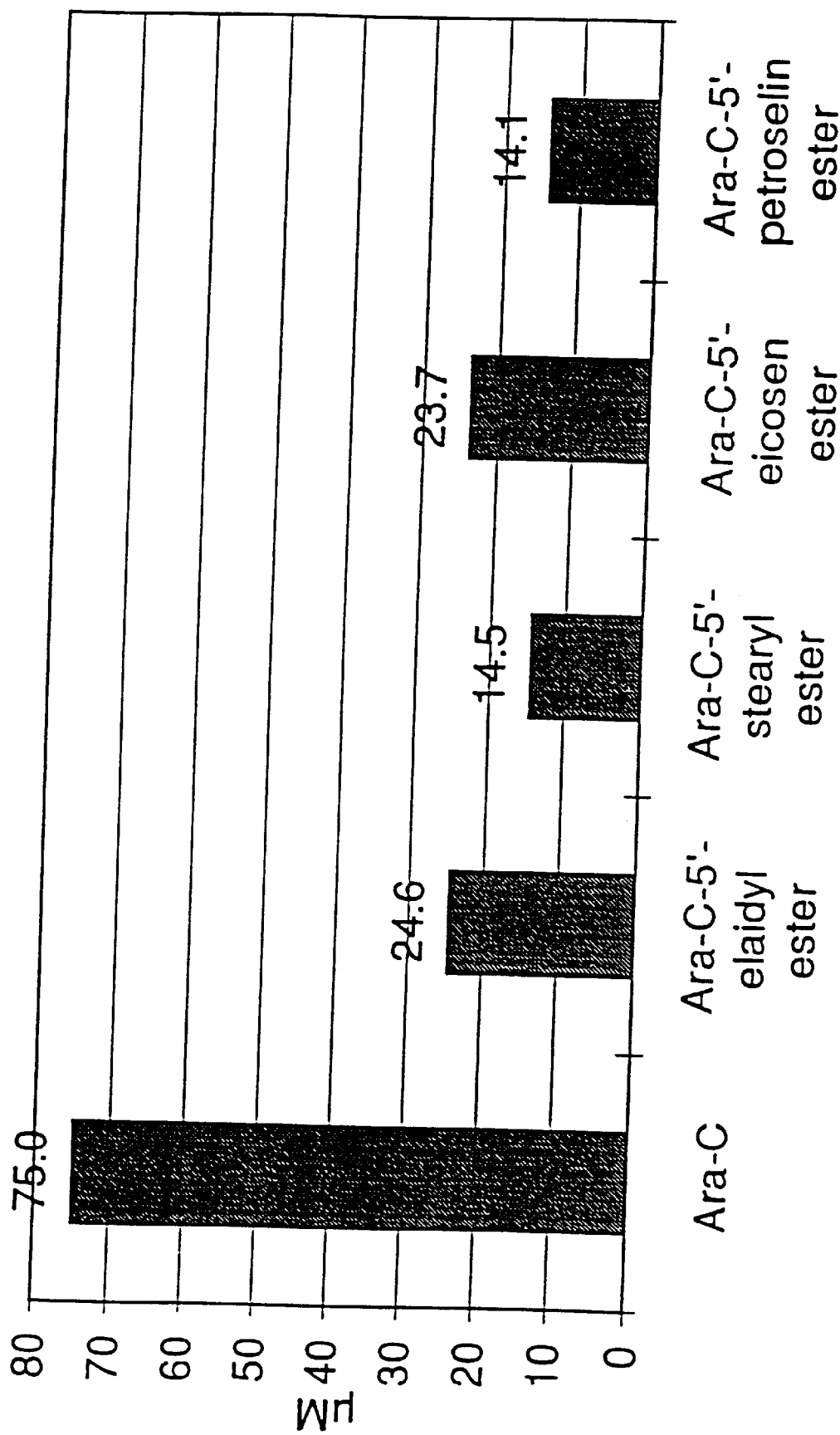
Figure 8:
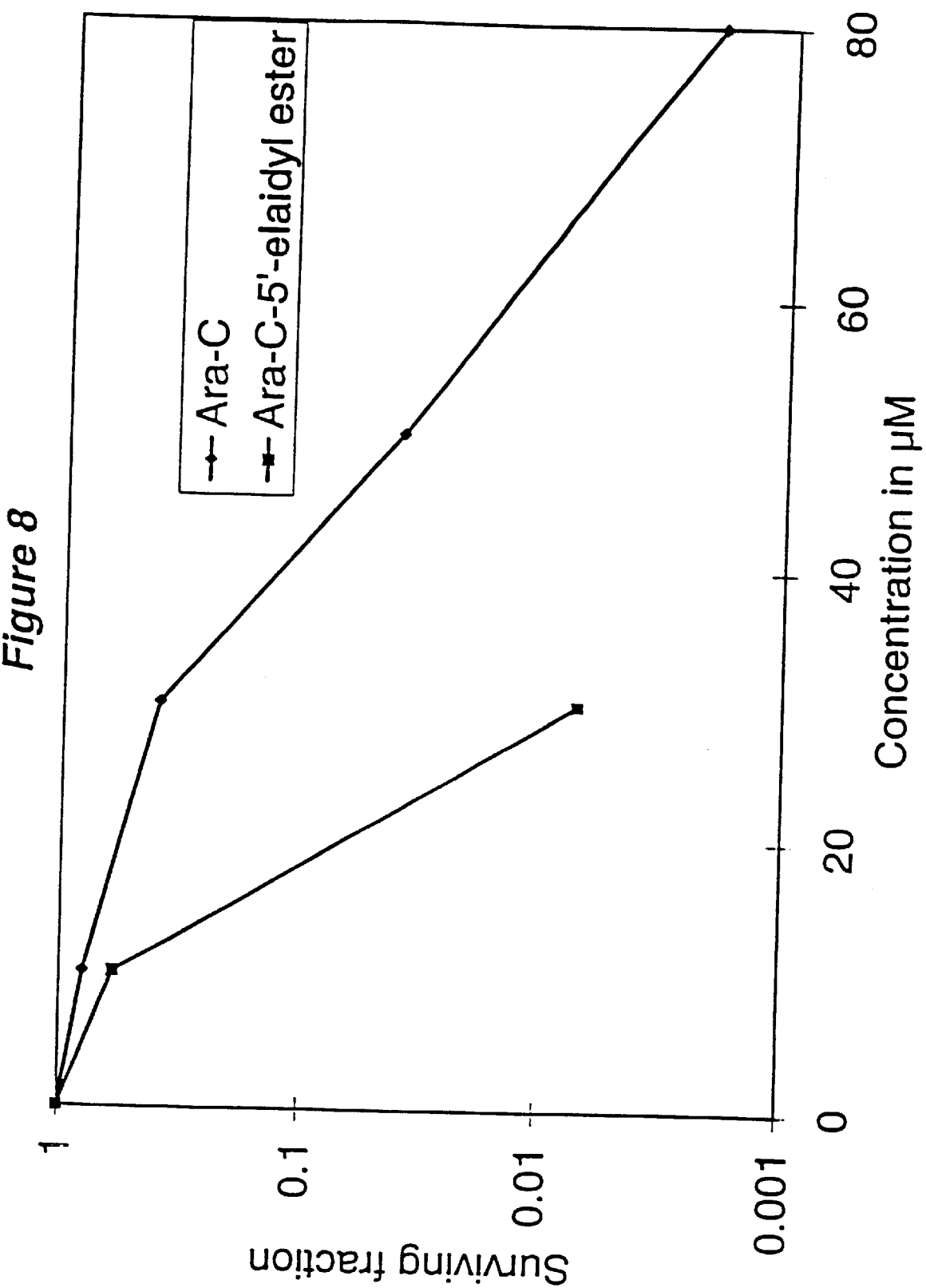
Figure 9:
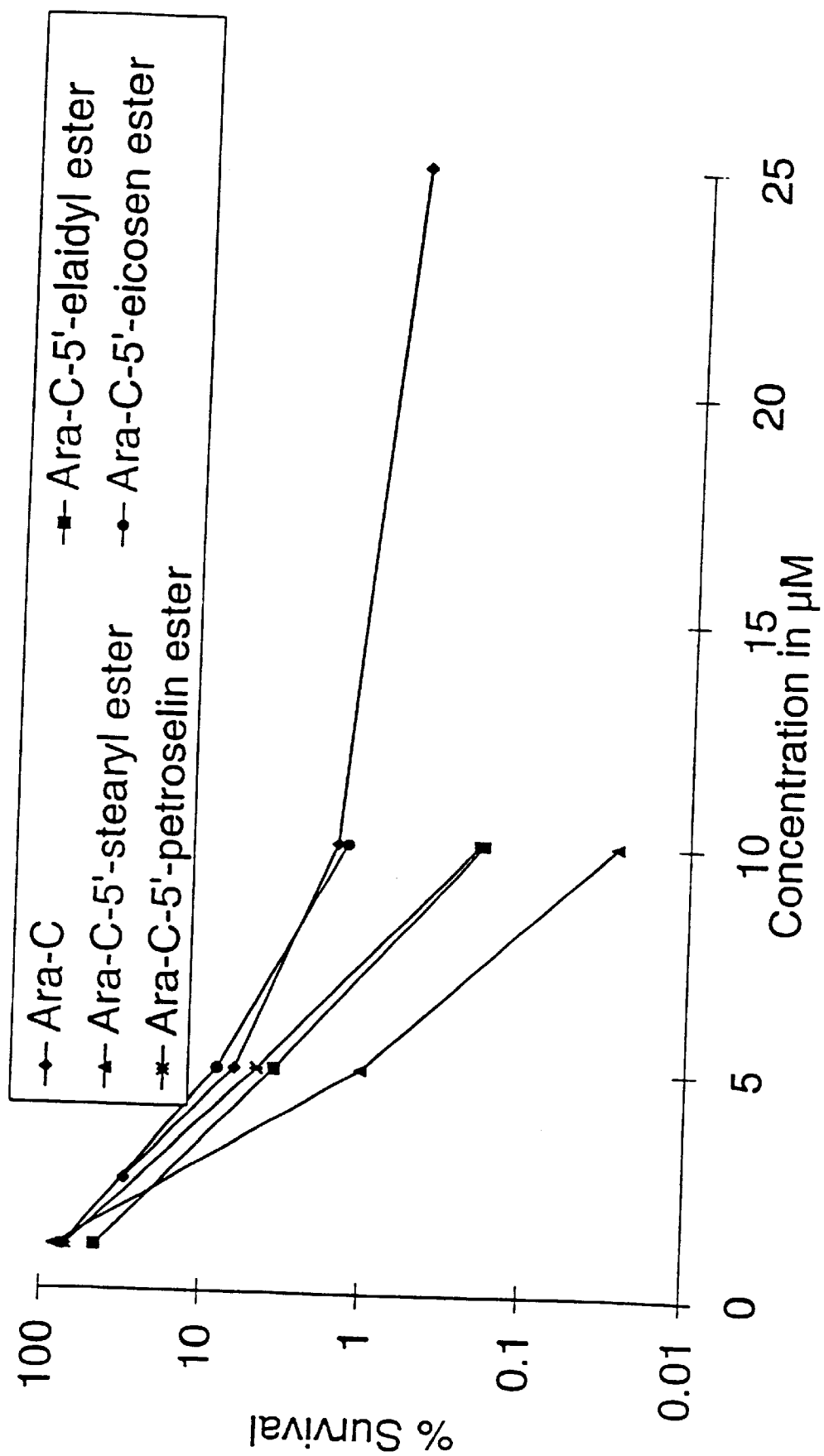

We have found, as shown in FIGS. 7, 8 and 9, that 3'- and 5'-O-esters of Ara-C and certain saturated and unsaturated fatty acids unexpectedly exhibit good activity against different tumours in contrast to Ara-C itself and also other mono- and diesters.

It is felt by the present inventors that the test model which is commonly used (injection of leukaemia cells into the abdominal cavity of mice and treated i.p.) is more comparable to an in vitro model than to an actual clinical situation and may have served to hide the particularly valuable properties of the selected Arab esters used in the present invention, as will be described below.

More specifically, the 3'- and 5'-O-esters which are used according to the present invention are those which are derived from $C_{18}$ or $C_{20}$ saturated and monounsaturated fatty acids.

Thus, the esters used according to the present invention may be represented by the formula 1:

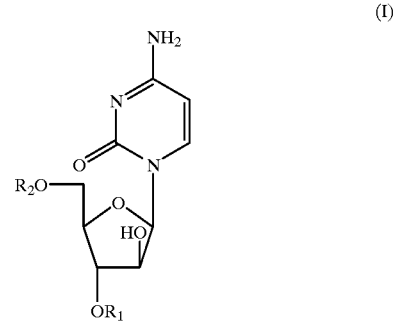

(I)

wherein $R_1$ and $R_2$ are independently selected from hydrogen, and $C_{18}$- and $C_{20}$- saturated and mono-unsaturated acyl groups, with the provisos that $R_1$ and $R_2$ cannot both be hydrogen.

The double bond of the mono-unsaturated acyl groups may be in either the cis or the trans configuration, although the therapeutic effect may differ depending on which configuration is used.

The position of the double bond in the mono-unsaturated acyl groups also seems to affect the activity. Currently, we prefer to use esters having their unsaturation in the ω-9 position. (In the ω-system of nomenclature, the position (ω) of the double bond of a monounsaturated fatty acid is counted from the terminal methyl group, so that, for example, eicosenoic acid ($C_{20}$:1 ω-9) has 20 carbon atoms in the chain and the single double bond is formed between carbon atoms 9 and 10 counting from the methyl end of the chain). Thus, we prefer to use Ara-C esters derived from oleic acid ($C_{18}$:1, ω-9, cis) elaidic acid ($C_{18}$:1, ω-9, trans) and eicosenoic acid ($C_{20}$:1, ω-9, cis) and ($C_{20}$:1, ω-9, trans) and stearic acid ($C_{18}$:0) and eicosanoic acid ($C_{20}$:0).

Both 3'-O- and 5'-O-monoesters and 3', 5'-O-diesters can be used in the treatment of different tumours in accordance with the present invention, but in general the 5'-O-monoesters are preferred. The 3',5'-O-diesters are expected to be useful in those cases where lipophilic properties are of advantage, e.g. absorption or uptake in lipid tissues.

The compounds of formula (I) wherein $R_1$ and $R_2$ are independently selected from hydrogen, elaidoyl, oleoyl. stearoyl, eicosenoyl (cis or trans) and eicosanoyl, with the provisos that $R_1$ and $R_2$ cannot both be hydrogen, oleoyl or stearoyl, $R_1$ cannot be hydrogen when $R_2$ is oleoyl or stearoyl, and $R_2$ cannot be hydrogen when $R_1$ is elaidoyl, oleoyl or stearoyl, are new compounds not previously reported in the prior art.

More specifically these new compounds of formula (1) are defined in the below Table A wherein $R_1$ and $R_2$ are as given:

TABLE A

| $R_1$ | $R_2$ |
|---|---|
| hydrogen | elaidoyl |
| hydrogen | eicosenoyl (cis) |
| hydrogen | eicosenoyl (trans) |
| eicosenoyl (cis) | hydrogen |
| eicosenoyl (trans) | hydrogen |
| eicosenoyl (cis) | eicosenoyl (cis) |
| eicosenoyl (trans) | eicosenoyl (trans) |
| eicosenoyl (cis) | eicosenoyl (trans) |
| eicosenoyl (trans) | eicosenoyl (cis) |
| eicosenoyl (cis) | elaidoyl |
| eicosenoyl (trans) | elaidoyl |
| elaidoyl | eicosenoyl (cis) |
| eiaidoyl | eicosenoyl (trans) |
| eicosenoyl (cis) | oleoyl |
| eicosenoyl (trans) | oleoyl |
| oleoyl | eicosenoyl (cis) |
| oleoyl | eicosenoyl (cis) |
| eicosanoyl | eicosanoyl |
| eicosanoyl | stearoyl |
| stearoyl | eicosanoyl |
| elaidoyl | stearoyl |
| eicosenoyl (cis) | stearoyl |
| eicosenoyl (trans) | stearoyl |
| elaidoyl | eicosanoyl |
| eicosenoyl (cis) | eicosanoyl |
| eicosenoyl (trans) | eicosanoyl |
| stearoyl | oleoyl |
| oleoyl | stearoyl |

A limiting factor for the use of Ara-C is its degradation by cytidine deaminase and deoxycytidine-monophosphate (dCMP) deaminase to inactive metabolites. We have surprisingly found that the monoesters of this invention are poor substrates for these deactivating enzymes. This difference could imply that these ester-derivatives are more suited than Ara-C itself for systemic or local treatment of malignant tumours, especially malignant tumours in the RES and CNS.

Figure 10:
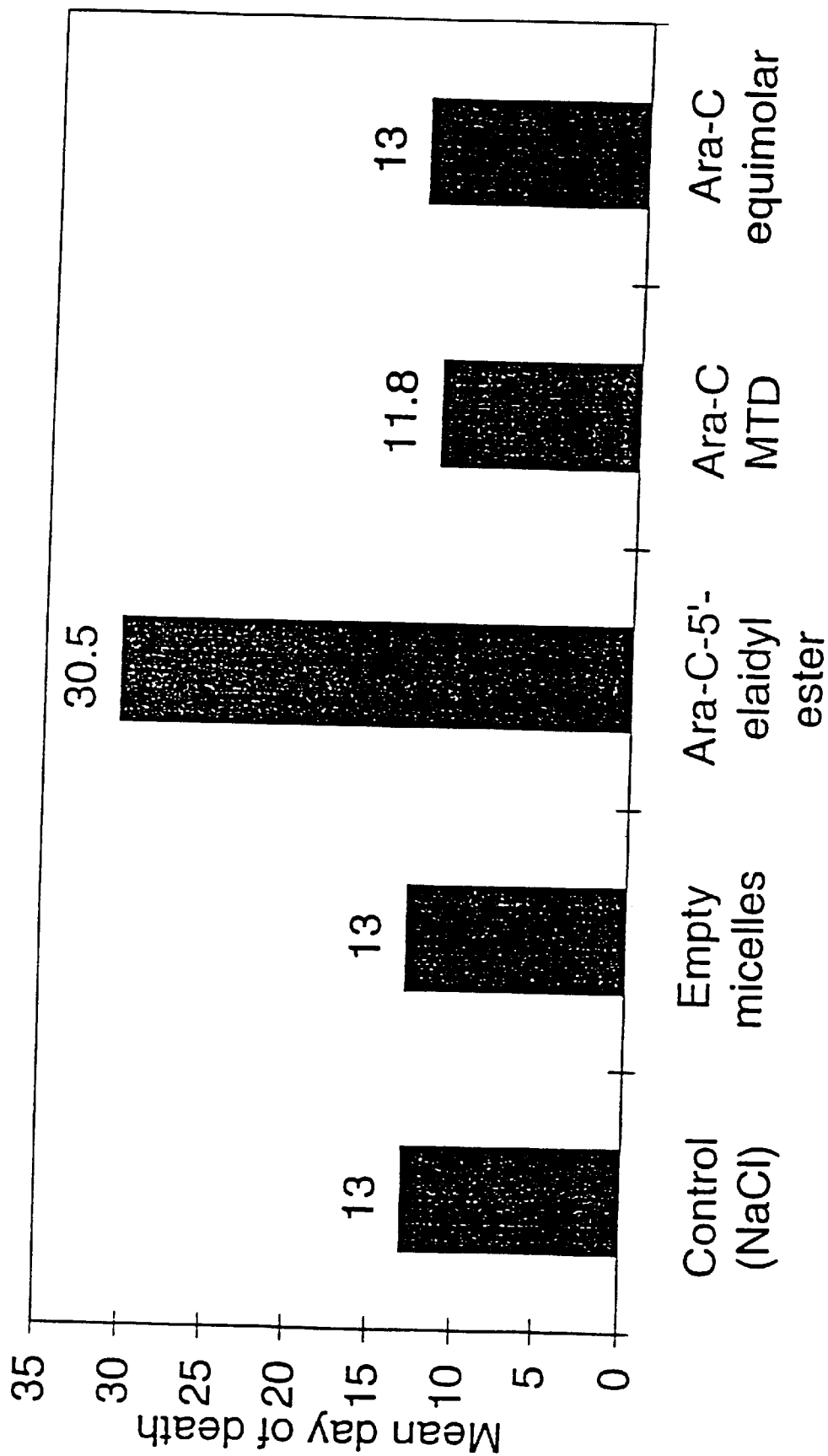
Figure 11:
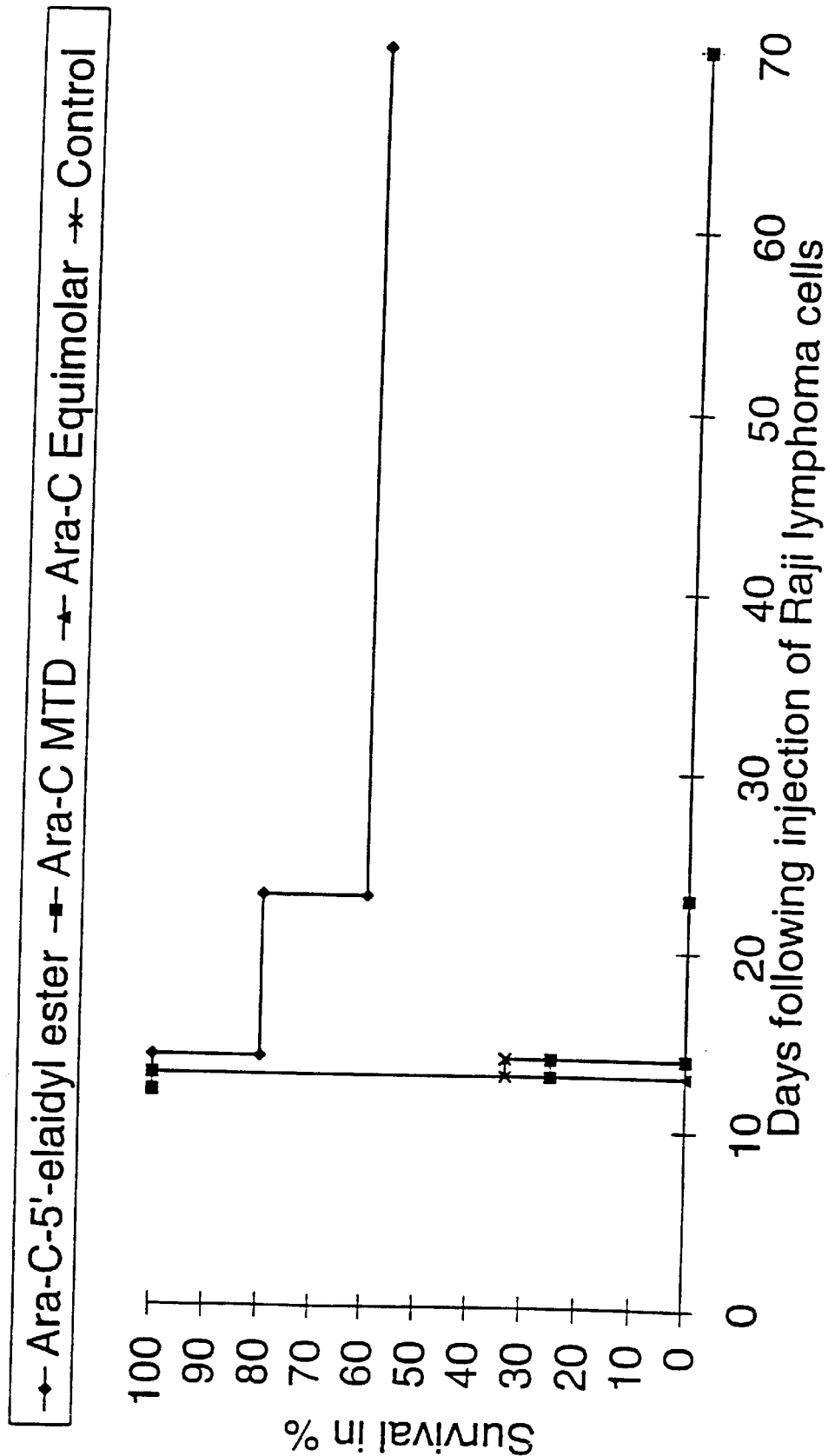
Figure 12:
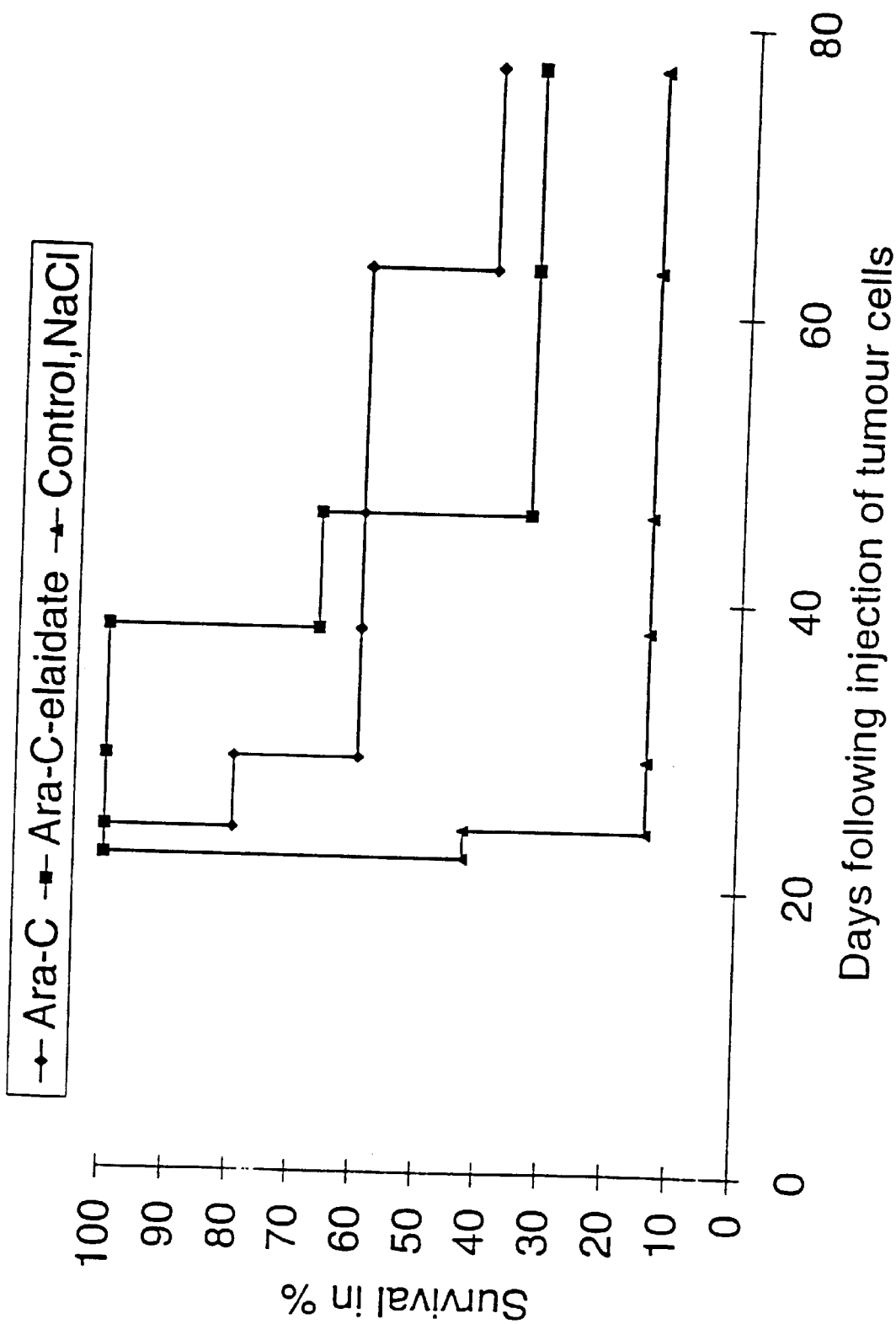

This is clearly demonstrated in the leukaemia brainmetastasis model described in FIGS. 10, 11 and 12 and especially with the more aggressive B-cell lymphoma shown in FIG. 11 were Ara-C itself is void of activity.

Figure 20:
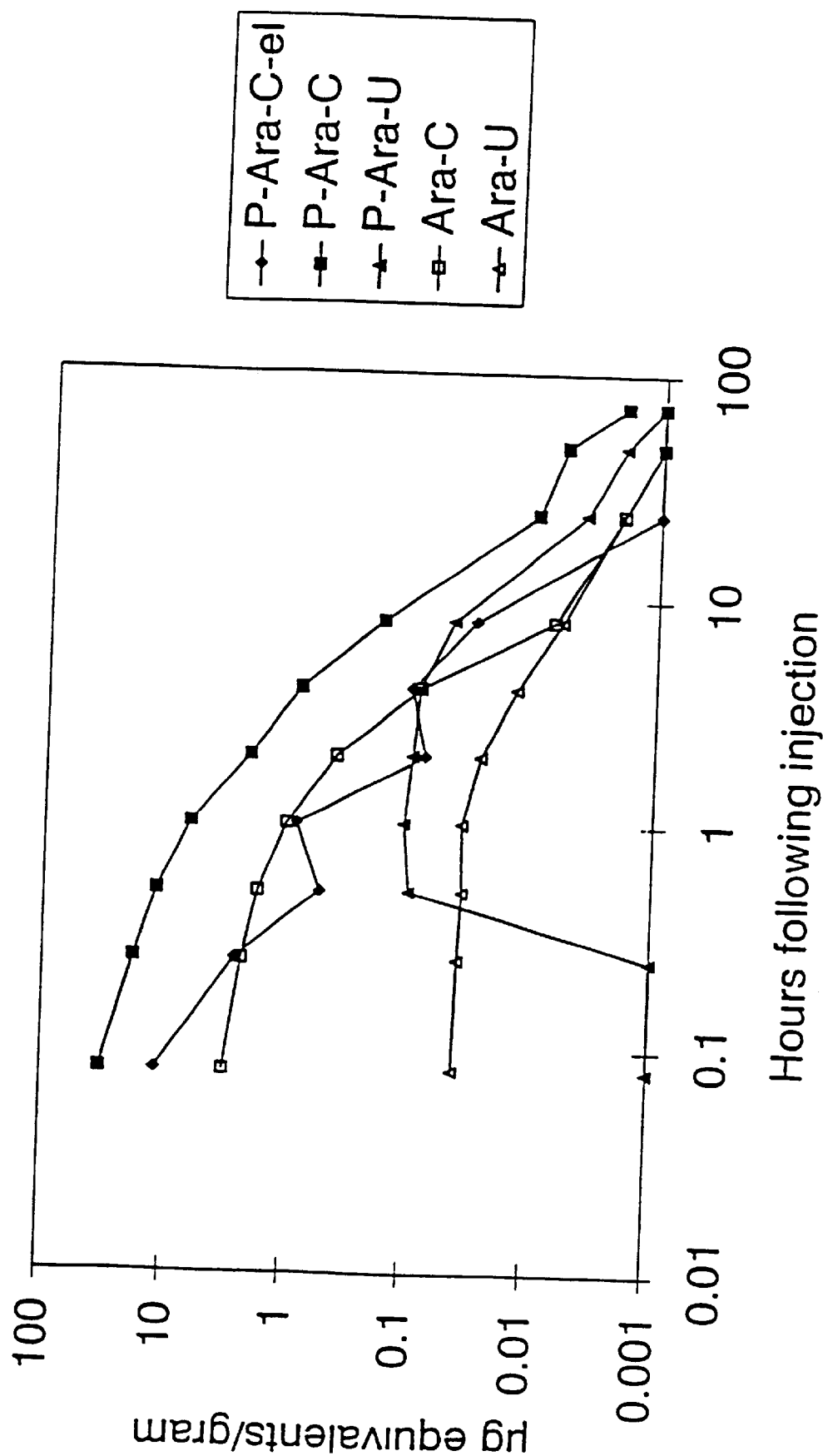

In the clinical treatment of myelogenous leukaemia, the rapid deactivation of Ara-C is compensated by continues infusion over 5–7 days to establish a reasonably stable therapeutic active plasma level of Ara-C. We have shown that following intravenous administration of equimolare amounts of radio labelled Ara-C and Ara-C-5'-elaidic ester to rats, a beneficial change in the metabolism rate and excretion profile is achieved. As can be seen from table 1 and FIG. 20, the administration of Ara-C-5'-elaidic ester gives both a higher initial whole blood and plasma concentration and a slower conversion to Ara-U. The deamination to Ara-U from Ara-C of the esters of this invention, here exemplified by administration as the elaidate is observed as significantly slower, and when the plasma levels of both Ara-C and Ara-U is below the assay limit of detection at 48 h when administered as pure Ara-C, the two compounds can still be quantified at 72 h following administration of Ara-C-5'-elaidate. As can be seen from table 2, the total excreted amount of Ara-U (AUC, 072 h) is the same for both administered compounds. In a clinical situation these results are reflected in a broader time window of therapeutic active concentration of Ara-C in the blood. In the in-vivo leukaemia model described in FIG. 13, Ara-C and the 5'-elaidic ester are compared, and similar anti-cancer effects achieved with Ara-C are demonstrated with administration of 1/20 of the molar dose of the ester.

If a similar toxicity profile that is seen in the dinic with Ara-C is observed with the ester derivatives, the improvement in therapeutic index should be of the same order (×20) of magnitude as the dose/effect improvement.

Figure 19:
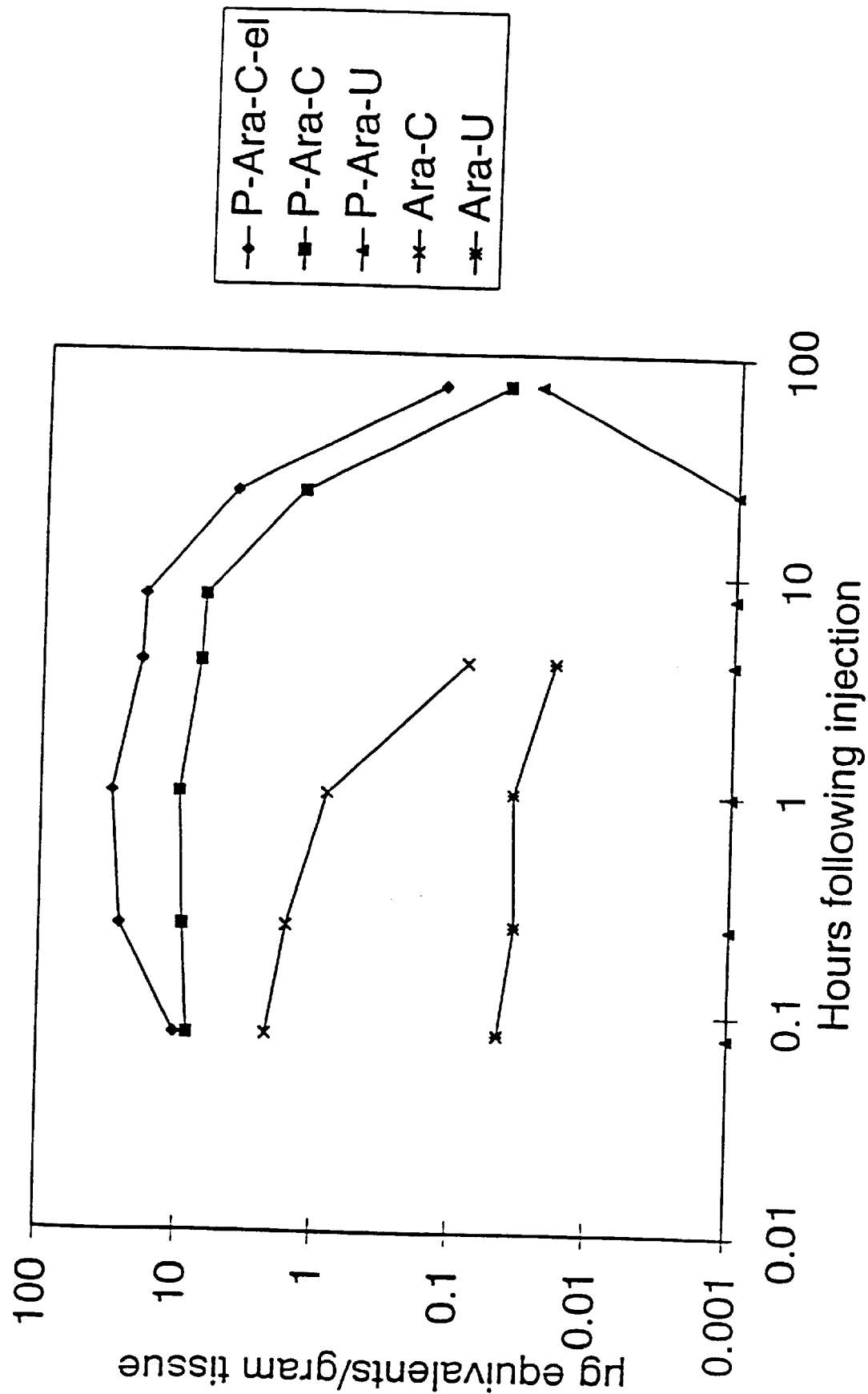
Figure 21:
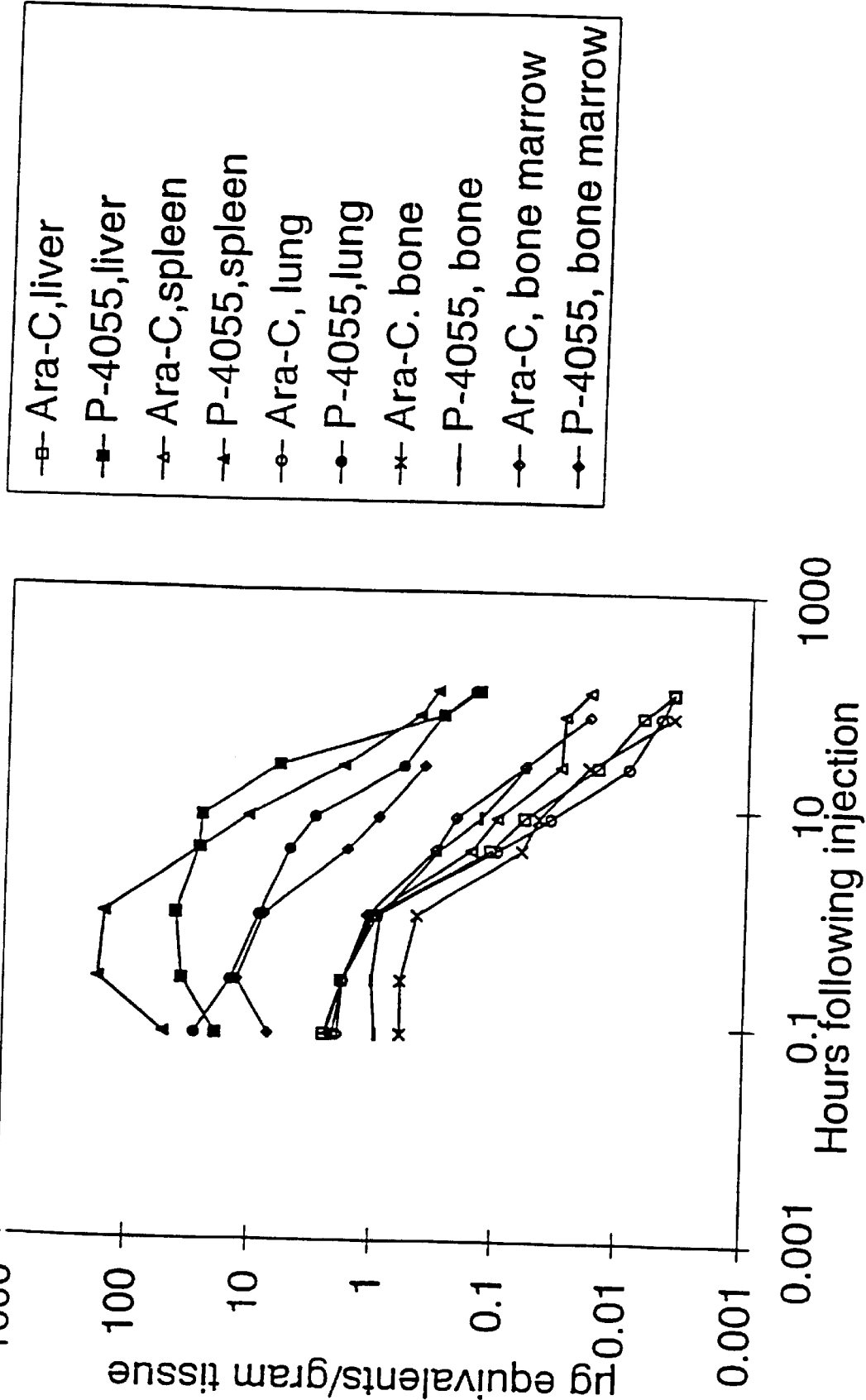

Of major importance in the treatment of leukaemia's and other diseases confined to the reticule endothelial system (RES) is of course the time window of active drug plasma concentration, but a localisation of the active compound in RES tissues (defined as liver, spleen, lymph, lung, intestine wall and free phagocytotic cells present in for example. bone marrow and whole blood) will be of great importance as well. We have observed (FIG. 21 and table 1) that by intravenous administration of equimolar amounts of Ara-C and Ara-C-5'-elaidic ester, the concentration of active drug in RES tissues is significantly higher, and persists with a broader time window when dosing the ester derivative. The pattern of distribution and metabolism is investigated in greater detail and results from the liver is given in FIG. 19. A therapeutic significant Ara-C level is sustained for at least 72 h after dosing the ester derivative. This can enable treatment of original liver cancer or liver metastases of colo-rectal, breast, melanoma or other forms of cancer. The treatment can stand as mono-therapy, or as paliative/adjuvant treatment in combination with surgery, radiation or other chemotherapy.

There is also observed increased concentrations of Ara-C in other tissues, and this combined with a smaller volume of distribution may open for therapy with Ara-C esters in cancer forms not normally associated with Ara-C treatment.

Moreover we unexpectedly found that the esters of this invention (FIG. 15) stimulated to a large degree the activation of NFkappaB whilst Ara-C gave no stimulation. The stimulation is a biological effect not normally seen with therapeutic chemicals, and in particular not with conventional cytostatics. This could suggest that the Ara-C esters of this invention have a stimulating effect on certain immune factors which again could explain the astonishing improvement in anti-cancer effect. This could be of significant importance in the treatment of neoplastic diseases involving immunocompetent cells such as leukaemia's and lymphomas.

The development of resistant cancer cells is a severe problem in the current chemotherapy of cancer. We have found (FIGS. 7–9) that the Ara-C derivatives of this invention show the same effect against Cis-platin resistant cells (NHIK 3025/DDP) and MDR resistant cells (A549) as against the corresponding non resistant cell lines. This, we believe, is because the derivatives are not substrates for the cellular drug-eflux mechanisms, such as the "gp 120 MDR pump", responsible for the phenomenon seen as multi drug resistance.

The $C_{18}$ and $C_{20}$ mono- and di-esters of Ara-C can be used according to the present invention in the treatment of a number of neoplastic tumours. We have found an especially promising effect on brain tumours such as glioma, and metastasis from other tumours such as sarcomas, carcinomas. as well as leukaemia. Currently, glioma are treated by surgery, radiation therapy and cytostatica, e.g. N,N-cis(2-chloroethyl)N-nitroso-urea (BCNU). However, the prognosis by these treatments is very poor.

Useful effects with the Ara-C esters of the present invention have also been found in metastatic tumours, such as carcinoma, sarcomas, leukaemia and melanomas.

The scope of the invention and its essential and preferred features are as defined in the attached claims.

Biological Effects

Micellar Formulation

A 1 mg/ml micellar formulation is prepared by the 1:1 (w/w) mixing of Ara-C ester (in DMSO) and lecithin (in ethanol) in sterile water.

Clonogenic Agarose Assay[1]

A biopsy was taken from the patient and placed immediately in a growth medium. Tumour tissue was desegregated mechanically, and living cells were selected the chemotherapeutic test substance was added, BCNU (in water) and Ara-C and Ara-C esters (in micelles), and the cells were cultivated in a soft agarose medium. Twenty-four hours before termination of the cultures (7 days) $^3$H Thymidin was added. The activity of the test substance is thus quantified as cpm in a scintillation counter.

[1] G. Unsgaard et al., Acta Neurochir (Wien) (1988) 91:60–66.

FIG. 1

The results here are obtained with a glioblastoma taken from a patient. The same response pattern is found in 8 other glioblastoma biopsies. The graph shows the in vitro comparison of Ara-C and its 3'-elaidyl ester and 5'-elaidyl ester. The results are given as % of the untreated control. A count of 50% ($CD_{50}$) is taken as promising regarding use in therapy of this actual cancer line. What is worth nothing here is the $10^{1.5}$ higher concentration of Ara-C needed to obtain $CD_{50}$ as compared with elaidyl esters.

FIG. 2

Figure 2:
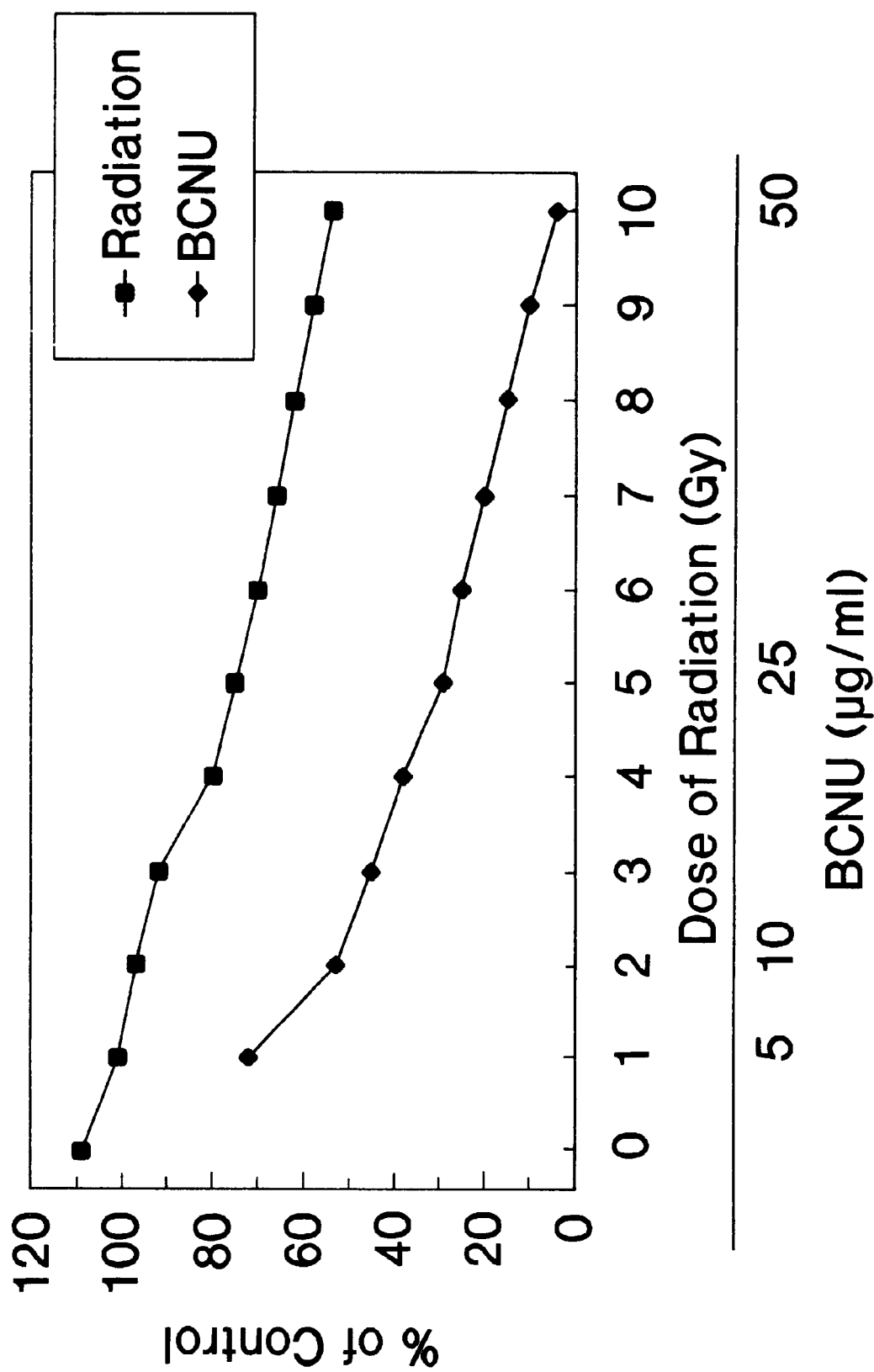
Figure 3:
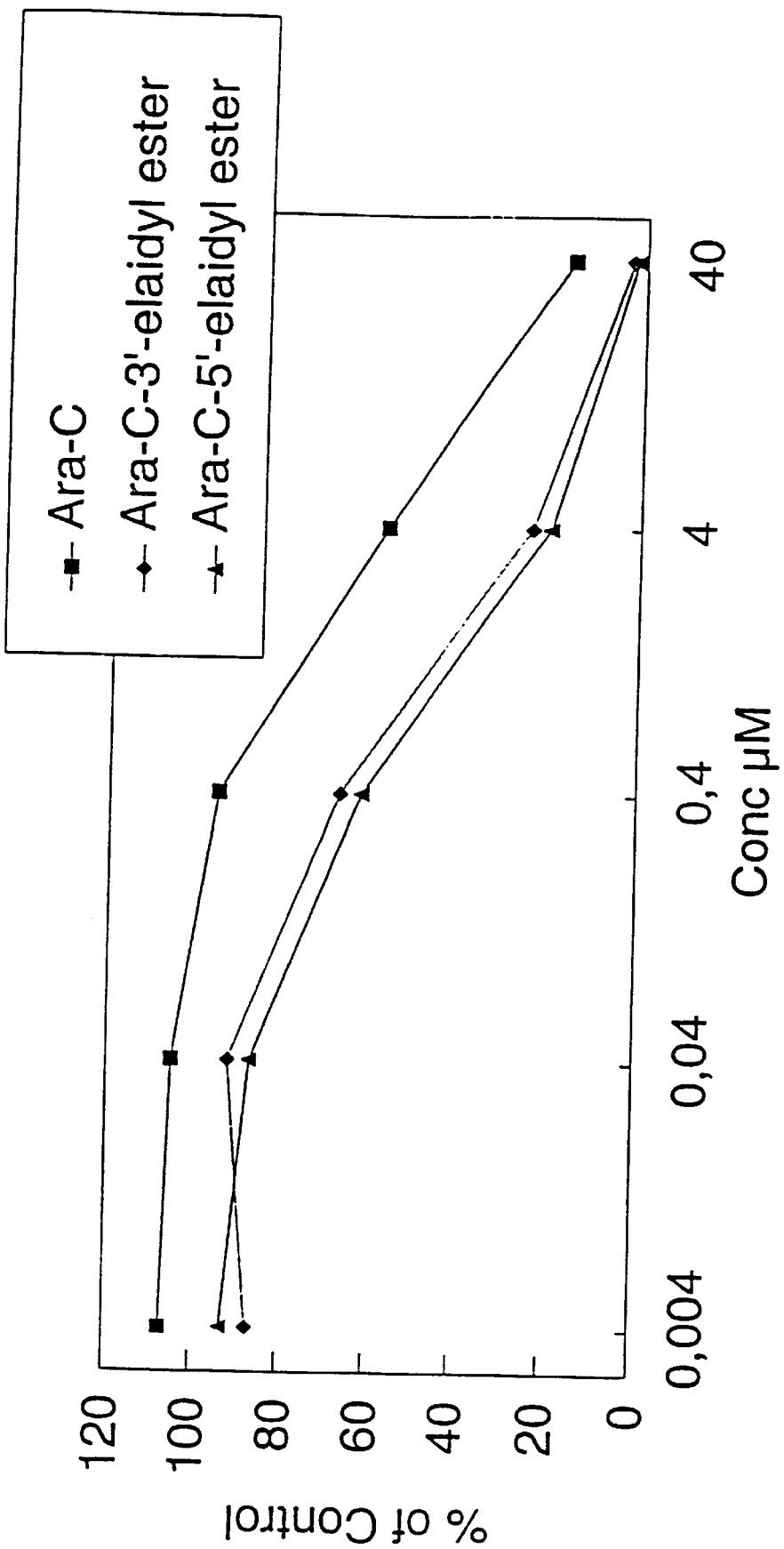
Figure 4:
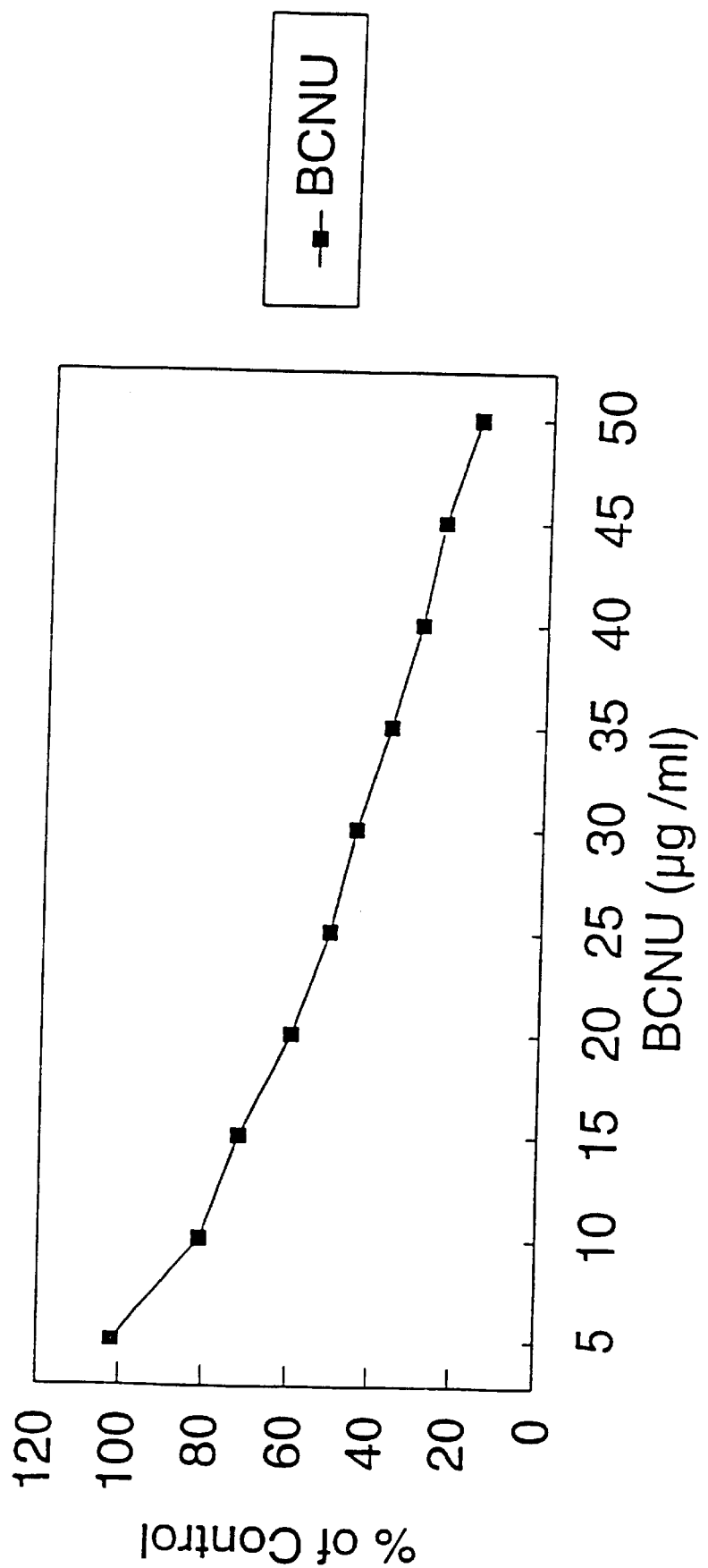
Figure 5:
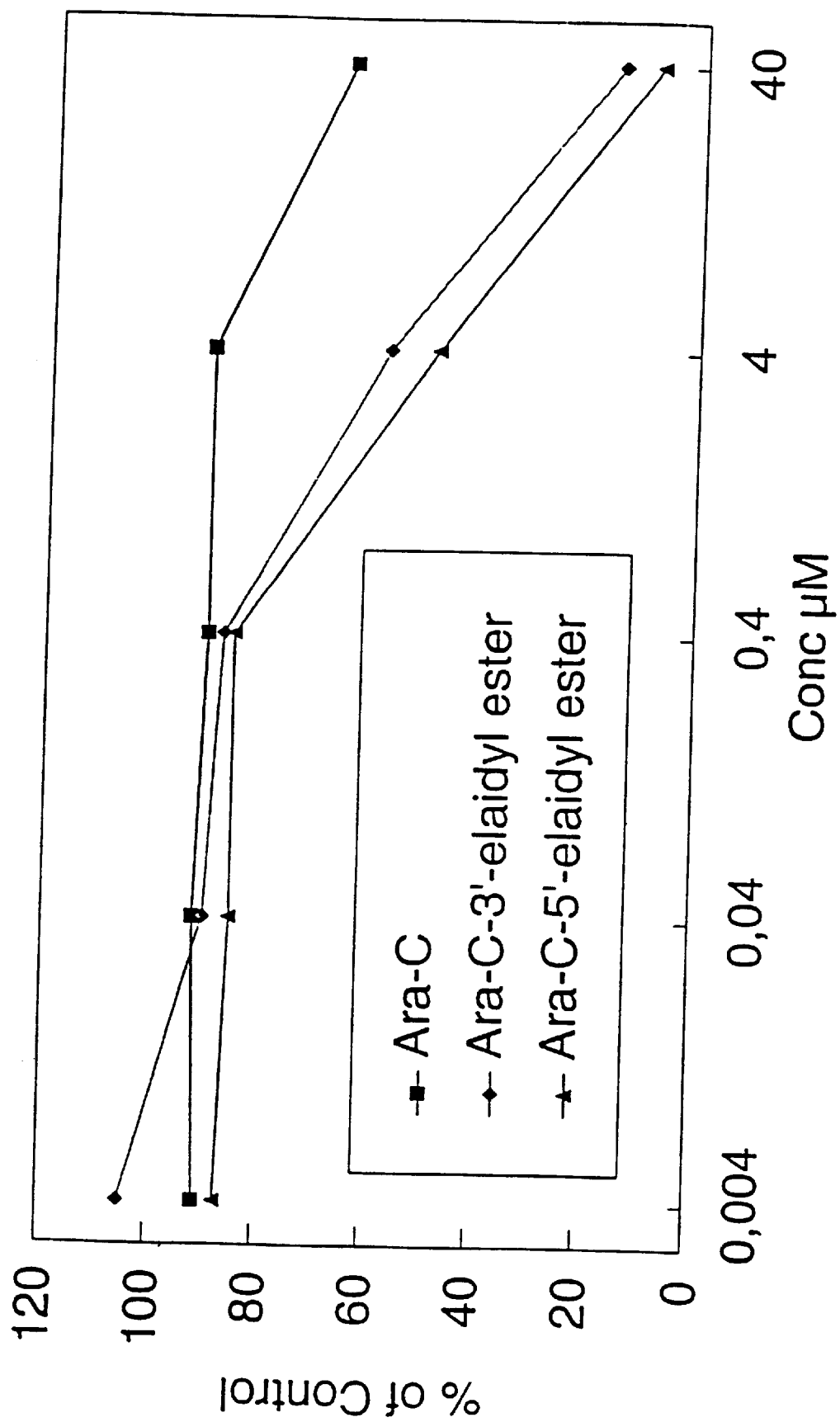
Figure 6:
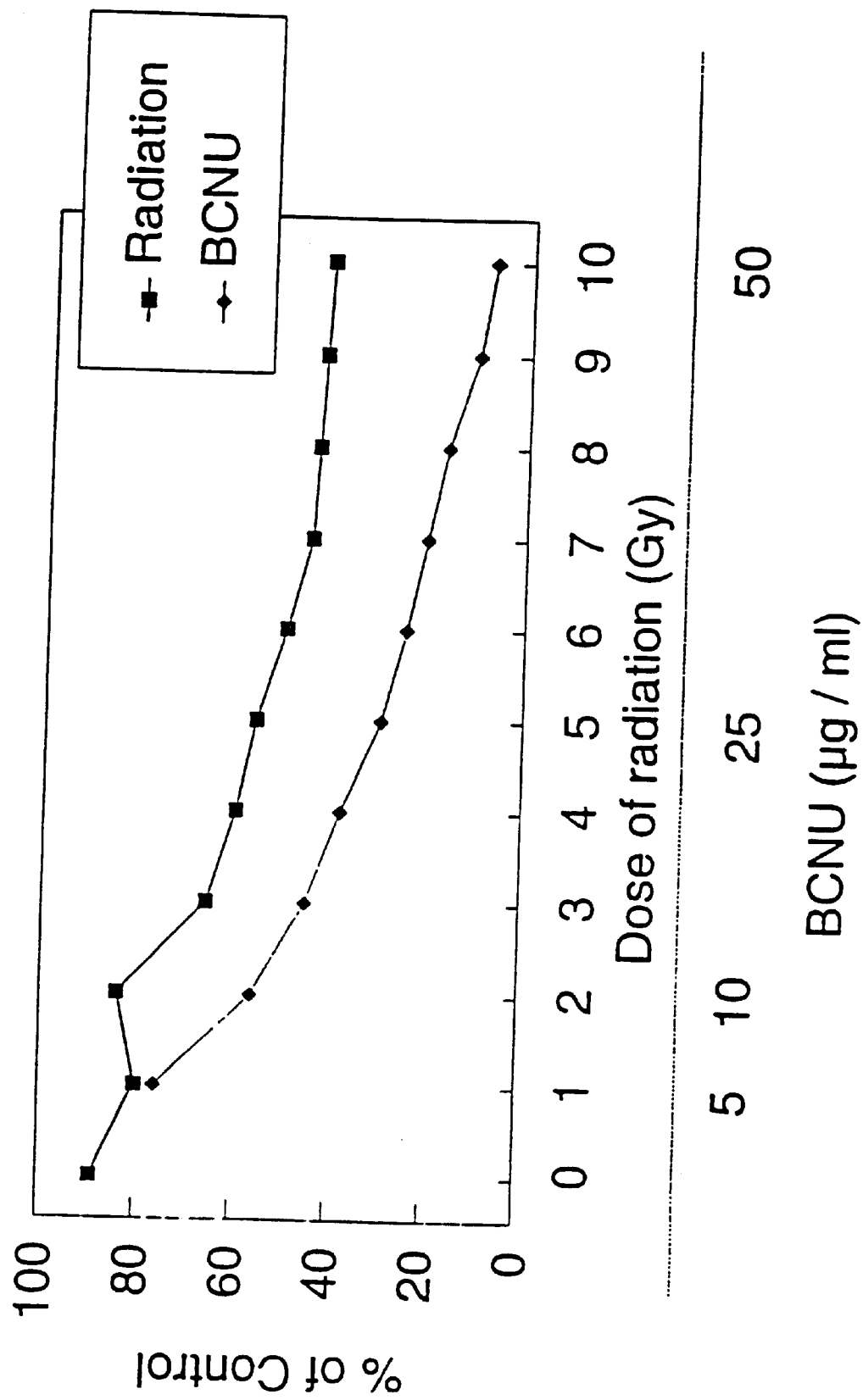

Shows the results obtained with the same glioblastoma as FIG. 1. The graph compares radiation therapy and chemotherapy (BCNU). A radiation dose greater than 10 Gray (Gy) needed to obtain $CD_{50}$ is in no sense practical in therapy. Comparing FIGS. 1 and 2, the concentration needed of BCNU to obtain $CD_{50}$ is about 10 times higher than what is needed with the Ara-C esters, but reasonably comparable to Ara-C alone.

FIG. 3

These results are obtained with a biopsy taken from a brain metastasis of a melanoma. The difference here between Ara-C and the 3'- and 5'-elaidyl esters is not as pronounced as with the glioma, but is still of the order of 10 times higher.

FIG. 4

This shows the activity of BCNU on the melanoma cell line. Compared to the Ara-C esters the BCNU is here needed in more than $1 \times 10^2$ higher concentration to give $CD_{50}$.

FIG. 5

This graph shows results with brain metastasis of a carcinoma (lung). These cancer cells are more resistant to chemotherapy, but the difference between Ara-C and Ara-C esters are still present.

FIG. 6

These results with BCNU treatment of brain metastasis of a carcinoma (lung) which are presented here are similar to what has already been demonstrated with the other cell lines.

Regarding the different cell types investigated, there seems to be an explicit difference in activity between the Ara-C esters, Ara-C alone and BCNU. A potentiation of $1 \times 10^2$ is very promising for a therapy situation. The findings indicate that the 5' esters are somewhat more potent than the 3' esters.

Cell Inactivation—Colony Forming Ability

Cell inactivation measured by means of loss of ability to form colonies was determined for several compounds. Cells used were of the established human cell lines of cancer cervix in situ origin, NHIK 3025, NHIK 3025/DDP, a cis-DDP-resistant variant of the same or A549 cells (human lung carcinoma). The cells were exposed to the test compound for 4 up till 24 hours. Test compounds were administered as micellar solution. Number of colonies were counted after about 12 days of incubation.

FIG. 7

The graph shows the in vitro comparison of the test compounds Ara-C, Ara-C-5'-elaidyl ester, Ara-C-5'-stearyl ester, Ara-C-5'-eicosen ester and Ara-C-5'-petroseline ester. The results are given as the dose needed to reduce cell survival with 90% relative to untreated control. As seen from the graph, substantial higher inactivation of NHIK 3025 cells is observed following exposure to the esters compared to Ara-C itself. The dose modifying factor at the 10% survival level is in the range of 3 to 5 for the Ara-C-esters compared to Ara-C, which means that a 3 to 5 times higher dose is required of Ara-C to obtain similar reduced colony forming ability as that observed for the esters.

FIG. 8

The results here are obtained with 4 h treatment of NHIK 3025/DDP cells. Enhanced effect of Ara-C-5'-elaidate ester compared to effect of Ara-C is observed similar to the effect enhancement observed in NHIK 3025 cells. Enhanced effect does not depend on resistance to cis-DDP.

FIG. 9

The graph shows the in vitro results using A549 cells (human lung carcinoma cells) colony forming ability to compare the test compounds Ara-C, Ara-C-5'-elaidyl ester, Ara-C-5'-stearyl ester, Ara-C-5'-eicosen ester and Ara-C-5'-petroseline ester. The cells were exposed for 24 hours. The highest inactivation is observed for Ara-C-5'-stearyl ester, but enhanced effect is also observed for the elaidyl and petroseline esters.

Raii Human B-lymphoma Cells—Leptomeninpal Carcinomatosis Model in Nude Rats

The model used is a tumour model in nude rats for leptomeningal growth of tumours. $1 \times 10^6$ cells of the Bcell tumour line Raji were injected into the spinal fluid through cistema magna (c.m.). of 4–5 weeks old nude rats. The animals develop neurological symptoms after 12–14 days if untreated. Anaesthetised animals were treated intracerebrally with a 40 μl injection into cistema magna with 3 or 4 bolus injections. Treatment was started 1 day after cell inoculation. Test compounds were Ara-C-5'-elaidyl ester (in micelles) and Ara-C. Ara-C was administered both at maximal tolerable dose (MTD) and at an equimolar dose to Ara-C-5'-elaidyl ester. Control animals (treated with NaCl)

or empty liposomes (micelles without Ara-C esters) developed symptoms from the central nervous system after approximately 14 days.

FIG. 10

3 bolus injections with Ara-C-elaidate on day 1,2 and 4 increased the symptom free latency period by 135% as compared to Ara-C, with mean day of death delayed from day 13 till day 30.5, as seen in FIG. 10. One rat survived for more than 70 days, and was considered to be cured. No tumours were visible at necropsy on day 76. This increase in disease-free survival is superior to results obtained with other therapeutic alternatives tested in comparable models for different types of human tumours.

FIG. 11

Survival curves from an additional experiment with nude rats inoculated with Raji cells in the brain, treated with 4 bolus doses is shown in this figure. One daily bolus dose on day 1,2,3 and 4 were administered into cisterna magna. As in the previous experiment, no effects were observed for Ara-C, neither at maximal tolerable dose of Ara-C (MTD) nor at a dose equimolar to Ara-C-elaidate. The results for the group given Ara-C-elaidate were even more astonishing than in the previous experiment 3 out of 5 rats were still alive and symptom-free at day 70. They were considered to be cured. This is most promising 5/6 control rats died on day 13. The 6th control rat had no backflow of spinal fluid into the syringe following injection of tumour cells and no neurological symptoms after 70 days. According to normal procedure this animal is left out of the results.

Molt 4 Human Lymphoma Cells—Leptomeningal Carcinomatosis Model in Nude Rats

The model used is a tumour model in nude rats for leptomeningal growth of tumours. $10^6$ cells of the T-cell tumour line Molt 4 were injected into the spinal fluid through cisterna magna (c.m.) of 4–5 weeks old nude rats. The animals develop neurological symptoms after 20–22 days if untreated. Anaesthetised animals were treated intracerebrally with a 40 µl injection into cisterna magna with 4 bolus injections. Treatment was started 1 day after cell inoculation. Test compounds were Ara-C-5'-elaidyl ester (in micelles) and Ara-C. Ara-C was administered both at maximal tolerable dose (MTD) and at an equimolar dose to Ara-C-5'-elaidyl ester. Control animals (treated with NaCl) developed symptoms from the central nervous system after approximately 20 days.

FIG. 12

Survival as a function of time for rats injected in the brain with Molt 4 lymphoma cells, treated 4x in cisterna magna is shown in FIG. 12. In this initial experiment, onset of death was delayed for the animals receiving Ara-C-elaidate compared to animals receiving Ara-C or control. The number of animals per group were: Control (7), Ara-C-elaidate (3) and Ara-C (5).

Leukaemia Model Using Raii Human B-lymphoma Cells

Figure 13:
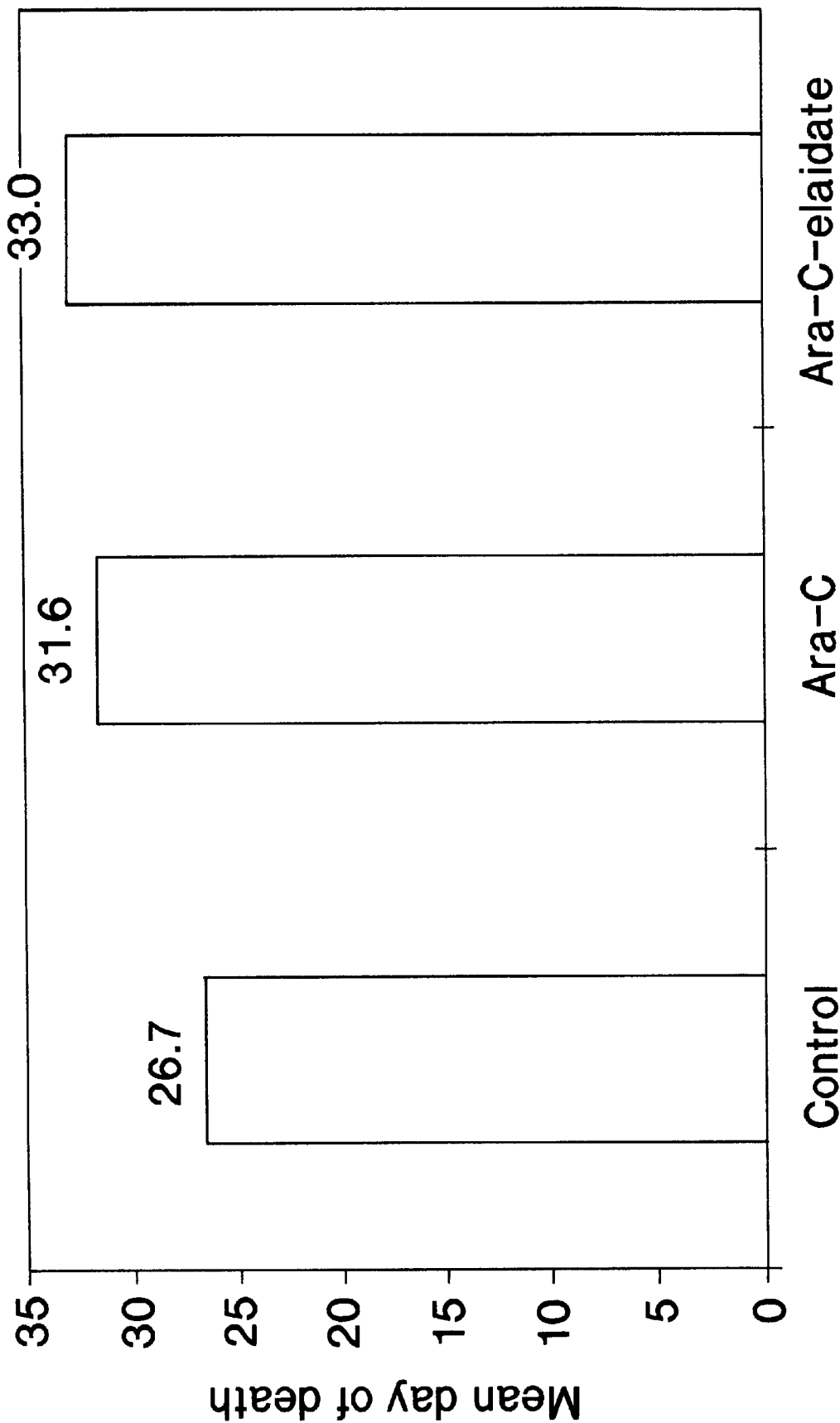
Figure 14:
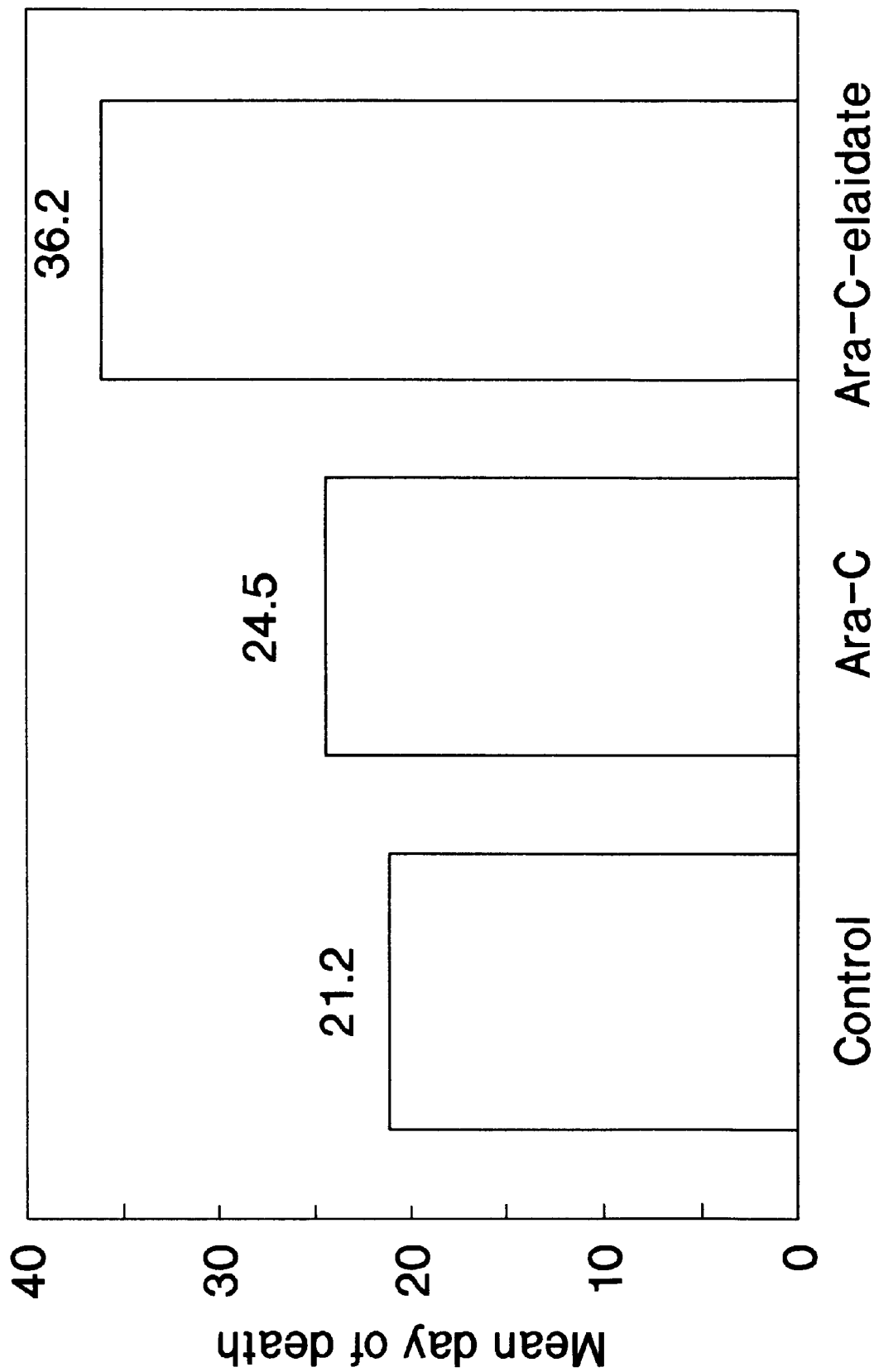

SCID mice were injected intravenously with $1 \times 10^6$ Raji human B-lymphoma cells. The mice were treated on days 7, 9, 11, 13 and 15 following injection of the tumour cells with either 20 mg/kg/day of Ara-C-elaidate or 200 mglkg/day of Ara-C or control. Animals develop paralysis of the hind legs as a result of the tumour growth. Mean day of death for the animals treated with the different treatments are shown in FIG. 13.

FIG. 13

Mean survival of SCID mice injected with Raii human B-lymphoma cells intravenously, treated intravenously with one injection on each of the days 7,9,11,13 and 15 with either Ara-C-elaidate, Ara-C or Control is shown in this figure. The doses were 20 mg/kg of Ara-C-elaidate and 200 mg/kg for Ara-C. On an equimolar basis, a 20 times reduced dose of Ara-C-elaidate compared to the Ara-C dose increased mean survival compared to control and Ara-C treated animals. The number of animals in each group were 7.

FIG. 14

Mean survival of SCID mice injected with Raji human B-lymphoma cells intravenously, treated intraperitoneally with once daily injection days 7–11 with either Ara-C-elaidate, Ara-C or Control is shown in this figure. The mean survival time is greatly prolonged for the Ara-C-elaidate when treatment is repeated daily instead of every other day.

Activation of the Cellular Transcription Factor NFkappaB

Human SW480 colon adenocarcinoma cells stably transfected with a CMV promotor/enhancer containing the gene for β-galactosidase were used. Activation of the transcription factor NFkappaB results in enhanced amount of the enzyme β-galactosidase in cytoplasma. The amount of β-galactosidase is quantified using optical density at 570 nm as parameter. The SW380 cells were incubated 2–3 days before exposure to the test compound for 4 h. The cells were washed and prepared, and optical density recorded for the different compounds.

FIG. 15

No β-galactosidase activity was measured following exposure to Ara-C, whilst a substantial increase in β-galactosidase activity was observed as an increase in optical density at 570 nm following exposure to Ara-C-elaidate. This indicates that a surprisingly high induction of the transcriptional activator protein NFkappaB is obtained with Ara-C-elaidate. NFkappaB is involved in gene control of a range of immune factors, and this activation by Ara-C-elaidate could explain the improved anticancer effects observed for Ara-Celaidate. One would expect a stimulation of certain immune cells by Ara-C-elaidate, which could be of special interest in the treatment of leukaemia and lymphomas.

The anti-tumour Activity of Ara-C-elaidate Versus Ara-C Against the Murine TLX/5 Lymphoma.

CBA mice weighing 20–25 g were inoculated subcutaneously inguinally with $1 \times 10^5$, TLX/5 tumour cells day 0. Ara-C-elaidate or Ara-C were administered intraperitoneally on days 3,4,5,6 and 7. Doses were in the range 6.25–50 mg/kg/day. There were 5 mice per treatment per group and 10 tumour-bearing controls. Activity was assessed in terms of increase in life span (ILS) versus controls.

FIG. 16

TLX/5 lymphoma tumour bearing mice and their % increase in lifespan (median of 5 per group) following treatment with Araelaidate or Ara-C, i.p treatment for 5 days is shown in this figure. Ara-C was only active at the dose 25 mg/kg, whilst Ara-C-elaidate was active at the doses 12.5 mg/kg and 25 mg/kg. Maximum increase in lifespan was 47.2% compared to 32.7% for Ara-C.

The Anti-tumour Activity of Ara-C-elaidate Versus Ara-C in SCID Mice Inoculated Intraperitoneally With Hemangiosarcoma Cells.

SCID mice were inoculated intraperitoneally with PV/2b/35 hemangiosarcoma cells. Mice were treated 5 days per week with 25 mg/kg/day of either Aras-C-elaidate prepared in micelles, Ara-C-elaidate dissolved in DMSO, Ara-C dissolved in PBS. Controls were empty micelles, DMSO or PBS respectively. The animals were not treated during weekends. Survival was the endpoint of the study.

FIG. 17

Survival of SCID mice inoculated intraperitoneally with PV/2b/35 hemangiosarcoma cells. Survival was greatly enhanced for animals treated with Ara-C-elaidate. The enhanced survival compared to control was observed both for Ara-C-elaidate prepared in micelles and for Ara-C-elaidate dissolved in DMSO.

FIG. 18

The results presented here are from a study of the 5'-Ara-C elaidyl ester in a glioblastoma tumour grown in nude mice. A glioblastoma cell line U-118 (Uppsala) tissue culture was injected subcutaneously in nude mice. A small part (2×2 mm) of growing tumour was transferred to new mice. The subcutaneous tumours show a somewhat different growth rate in the various animals, but at the size of 4–6 mm, an injection with a 10 mg/ml micellar solution of the Ara-C ester was given intratumourally. Depending on the actual tumour size, the animals received the same relative amount of test substance. The control was given saline water. The growth rate was recorded as relative tumour volume (RTV). The control tumour follows a quite normal growth pattern typical to this cancer type. What is noted is the complete stop in tumour growth of the treated animals. Further, the animals showed no signs of toxic side effects, which in the case of Ara-C are damage to bone marrow with the development of anaemia or haemorrhages, nor was there noted any sign of CNS disturbance.

Comparative Pharmacokinetic, Distribution, Metabolism and Excretion of $^{14}$C-Ara-C-elaidate and $^{14}$C-Ara-C Administered Intravenously to Male Rats $^{14}$C-Ara-C-elaidate (in micelles) or $^{14}$C-Ara-C were administered intravenously to male rats at equimolar doses, 5 mg/kg for $^{14}$C-Ara-C-elaidate and 2.4 mg/kg for $^{14}$C-Ara-C. Plasma concentrations of total radioactivity and of the metabolites were determined at different timepoints. Tissue concentrations of total radioactivity were determined from a range of tissues at different timepoints up to 120 hours following injection. Liver tissues were extracted and metabolite concentrations were determined up to 72 hours post injection. Tissue distribution of Ara-C-elaidate was significantly altered compared to the distribution of Ara-C. Maximal concentrations in most tissues were notably higher and occurred at later timepoints following $^{14}$C-Ara-C-elaidate administration, especially in whole-blood/plasma, spleen, liver and lungs. Maximal concentrations in muscle, salivary glands, skin and urinary bladder were lower. The proportion of the dose in whole-blood at 0.08 hours after $^{14}$C-Ara-C-elaidate administration was estimated to be 64.7%, notably higher than the proportion present in the systemic circulation at this time after $^{14}$C-Ara-C administration (7.76%). Excretion via the renal system was much slower for the elaidate than the Ara-C itself. Elimination from tissues were much slower for $^{14}$C-Ara-C-elaidate compared to elimination from tissues when $^{14}$C-Ara-C was administered.

Table 1

Maximal concentrations of radioactivity (expressed as μg equivalents/g) following administration of equimolar doses of $^{14}$C-Ara-C-eiaidate or $^{14}$C-Ara-C with corresponding timepoint for maximal concentration. As seen in the table, maximal concentrations occurred in different tissues and at different timepoints for the two compounds.

TABLE 1

| Tissue | $^{14}$C-Ara-C-elaidate ($t_{max.}$ hours) | $^{14}$C-Ara-C ($t_{max.}$ hours) |
|---|---|---|
| spleen | 175.2 (0.25) | 2.406 (0.08) |
| plasma | 55.60 (0.08) | 3.058 (0.08) |

TABLE 1-continued

| Tissue | $^{14}$C-Ara-C-elaidate ($t_{max.}$ hours) | $^{14}$C-Ara-C ($t_{max.}$ hours) |
|---|---|---|
| whole-blood | 47.32 (0.08) | 2.707 (0.08) |
| liver | 42.37 (1 hour) | 2.526 (0.08) |
| blood cells | 34.37 (0.08) | 2.201 (0.08) |
| lung | 28.97 (0.08) | 2.144 (0.08) |
| vena cava | 17.29 (0.08) | 1.887 (0.25) |
| bone marrow | 13.29 (1 hour) | 1.950 (0.08) |
| heart | 10.15 (0.08) | 1.916 (0.25) |
| kidney | 9.108 (0.08) | 7.752 (0.08) |
| prostate | 9.014 (4 hours) | 2.810 (0.25) |
| pituitary | 8.359 (0.08) | 0.931 (0.08) |
| aorta | 7.795 (0.08) | 2.213 (0.08) |
| urinary bladder | 6.421 (4 hours) | 13.07 (1 hour) |
| adrenal glands | 5.229 (0.08) | 1.764 (0.08) |
| salivary glands | 2.366 (0.25) | 2.505 (0.08) |
| lacrimal glands | 4.438 (4 hours) | 2.460 (0.08) |
| lymph nodes | 2.831 (1 hour) | 2.222 (0.08) |
| skin | 1.793 (0.25) | 2.189 (0.08) |
| muscle | 1.990 (0.25) | 2.158 (0.08) |
| pancreas | 2.817 (0.08) | 2.148 (0.08) |
| thymus | 2.090 (0.25) | 2.054 (0.08) |
| brain | 1.408 (0.08) | 0.233 (1 hour) |

Table 2

Excretion of radioactivity (% of dose) after intravenous administration of $^{14}$C-Ara-C-eladiate (5 mg/kg) or $^{14}$C-Ara-C (2.4 mg/kg) to male rats. Rate of excretion of radioactivity in urine is slower for $^{14}$C-Ara-C-eladiate than for $^{14}$C-Ara-C.

TABLE 2

| Sample/time (hours) | $^{14}$C-Ara-C-elaidate | $^{14}$C-Ara-C |
|---|---|---|
| 0–6 | 59.1 ± 3.7 | 85.3 ± 3.1 |
| 6–24 | 34.1 ± 2.5 | 8.8 ± 1.9 |
| 24–48 | 2.7 ± 0.8 | 0.5 ± 0.3 |
| 48–72 | 0.5 ± 0.1 | 0.2 ± <0.1 |
| 72–96 | 0.2 ± 0.1 | 0.2 ± 0.1 |
| 96–120 | 0.1 ± <0.1 | 0.1 ± 0.1 |

FIG. 19

Figure 15:
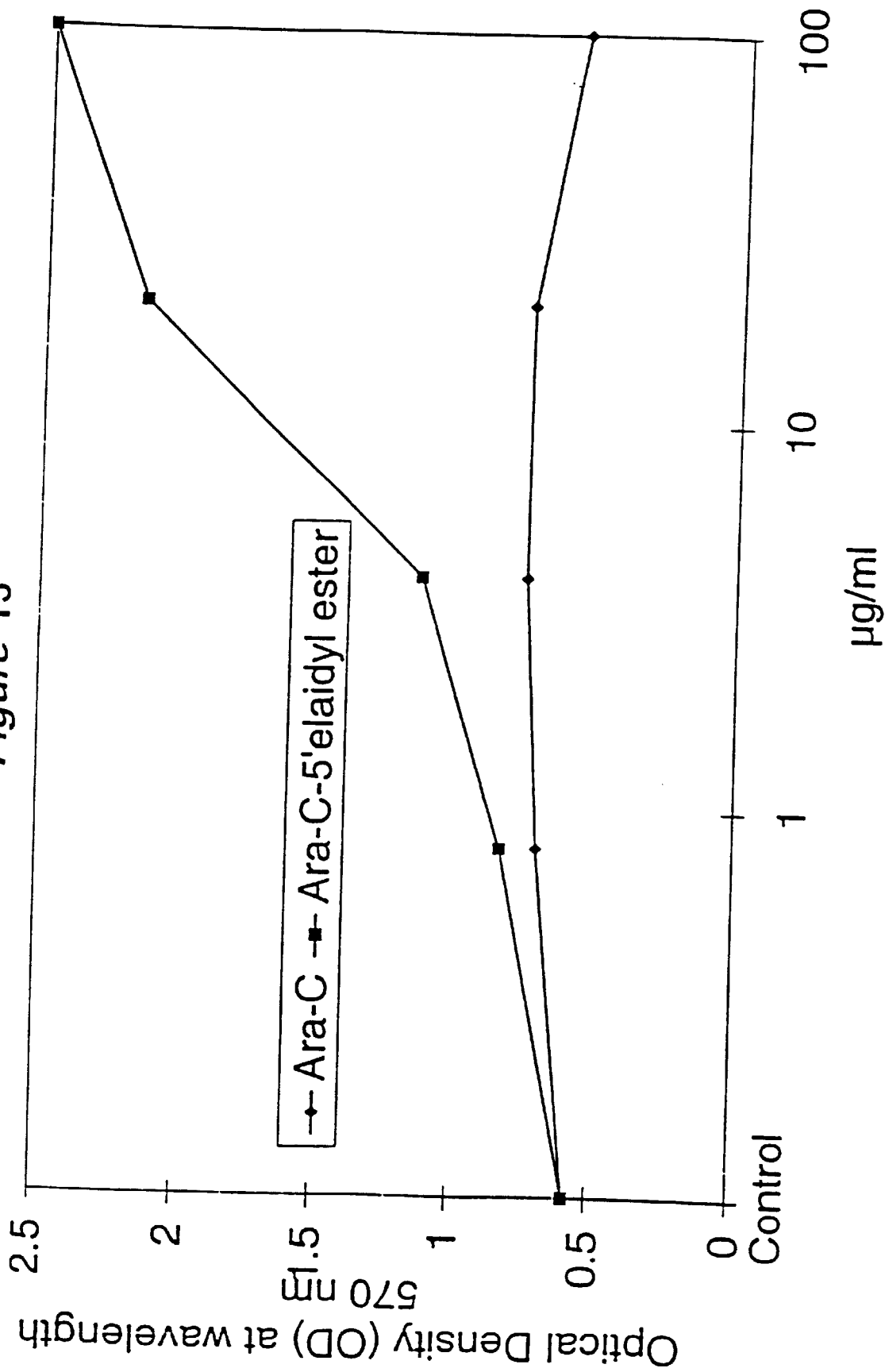
Figure 16:
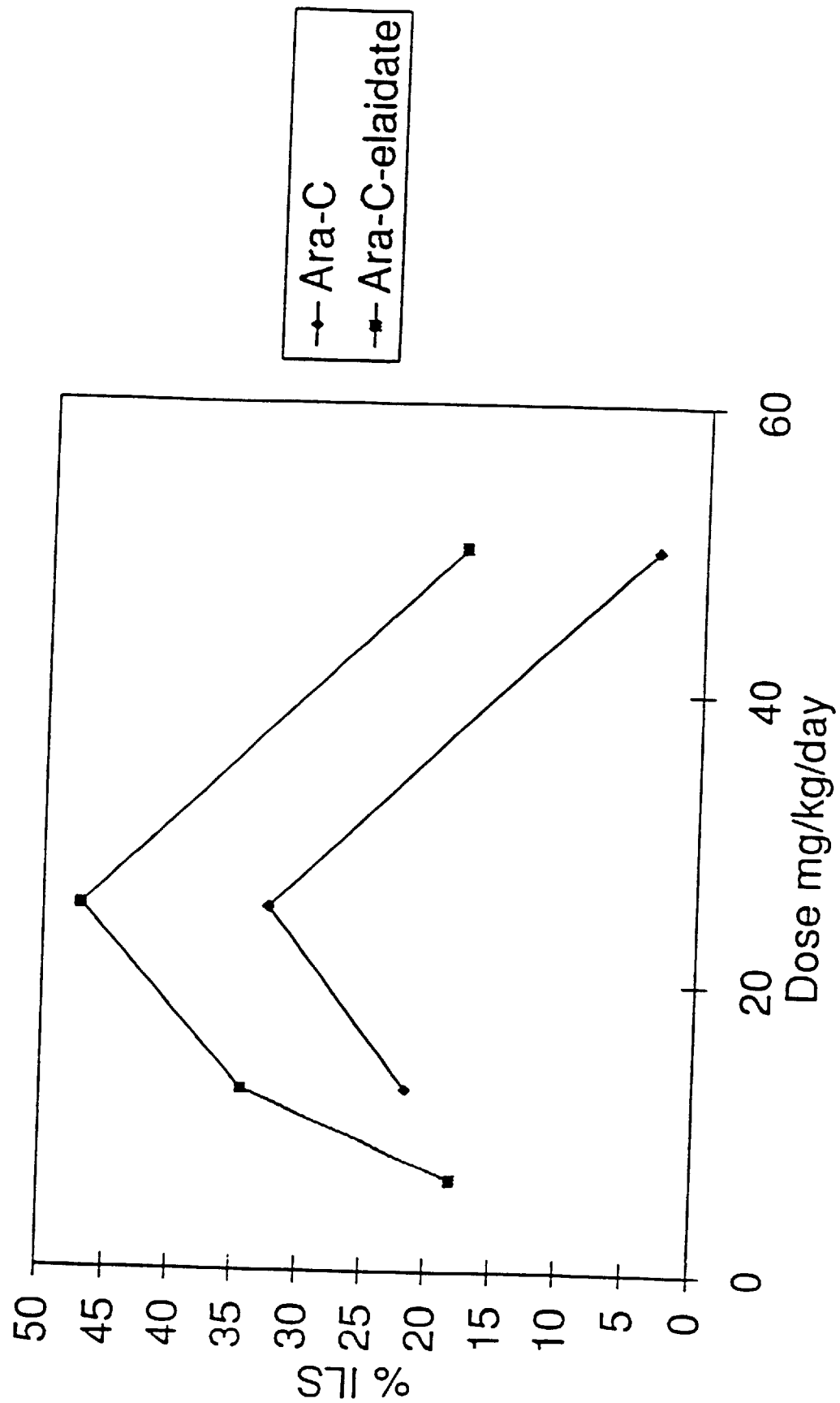
Figure 17:
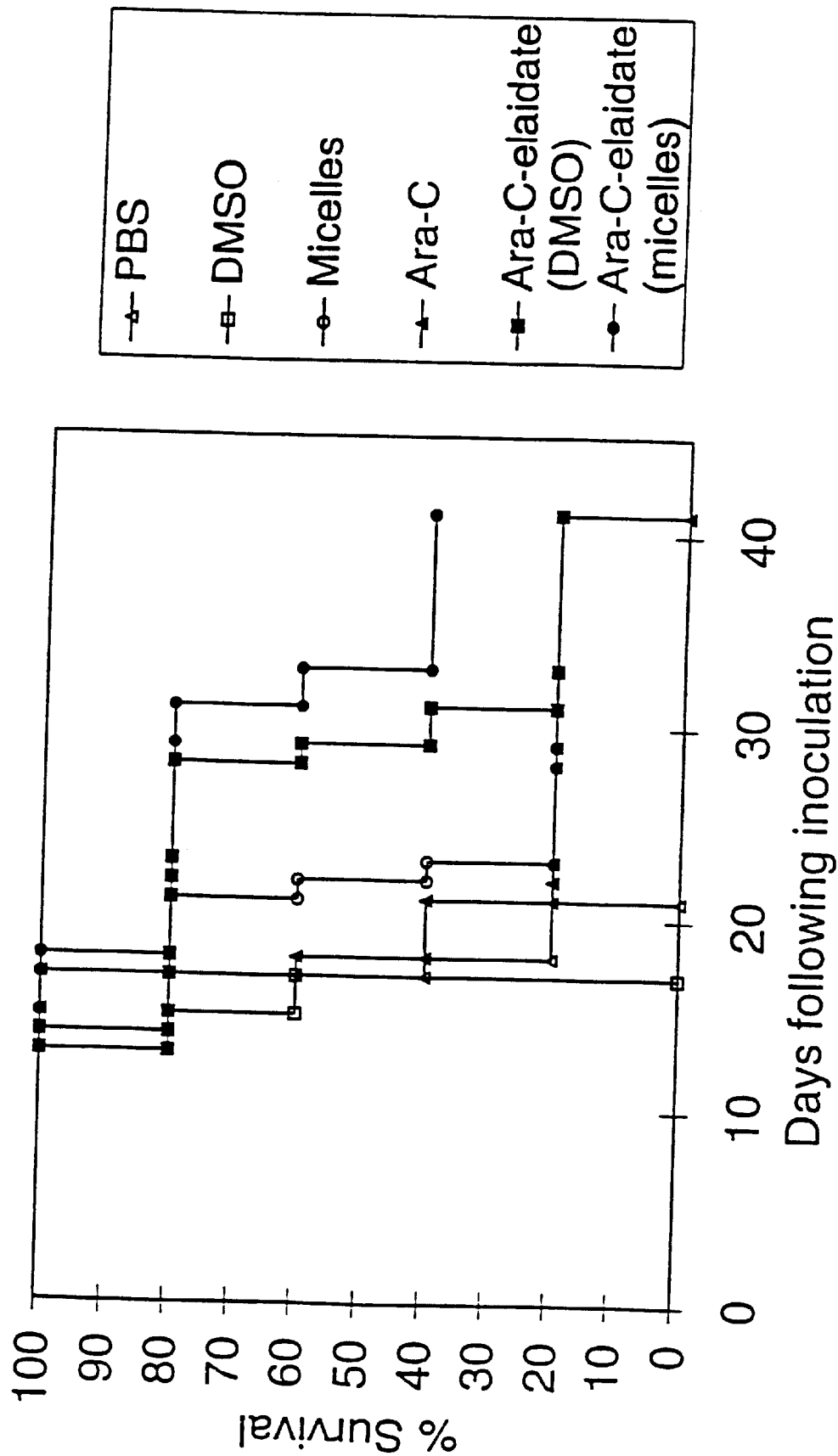
Figure 18:
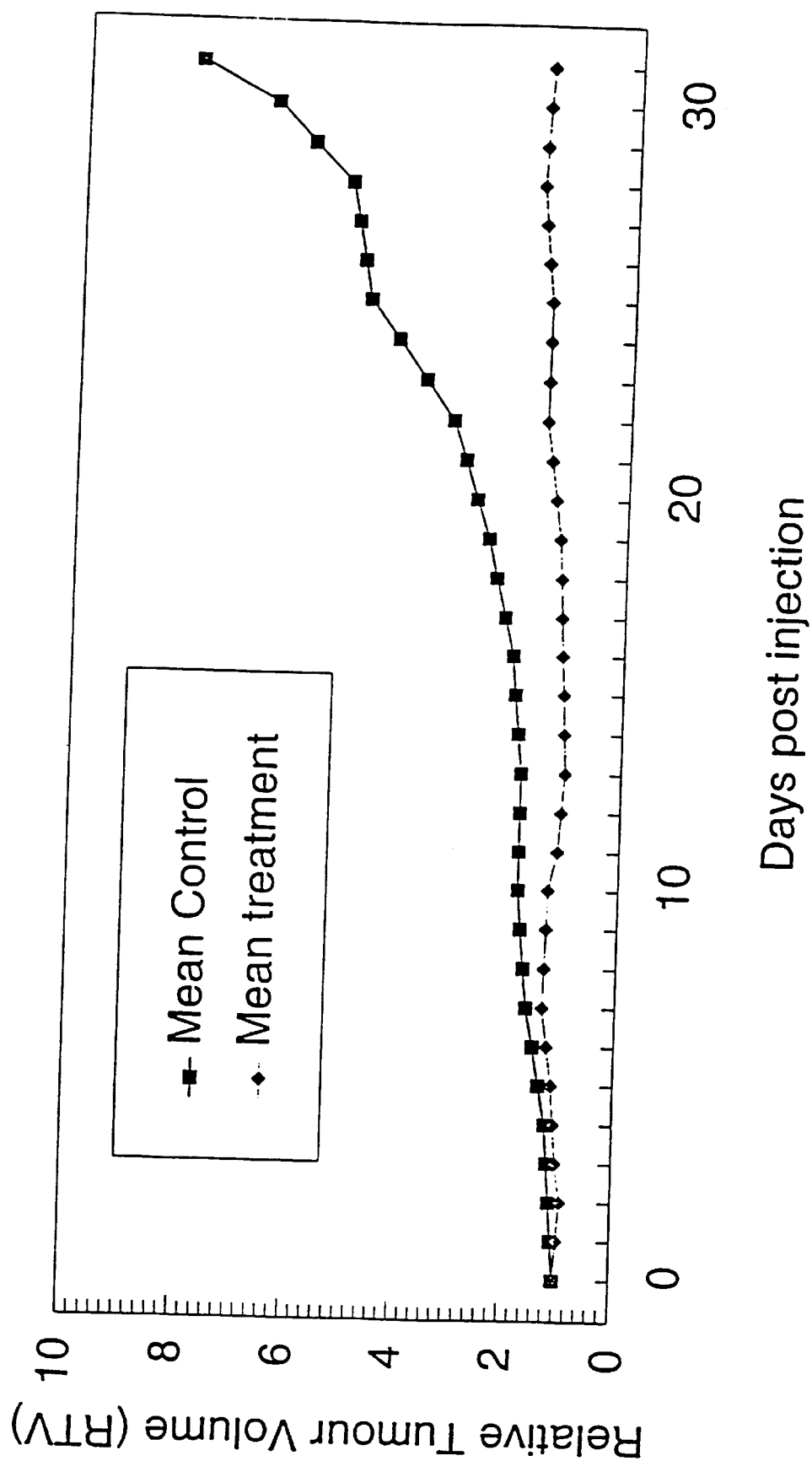

Liver concentration of Ara-C-elaidate (P-Ara-C-el) and the metabolites Ara-C (P-Ara-C) and Ara-U (P-Ara-U) are plotted as a function of time following injection of $^{14}$C-Ara-C-elaidate in FIG. 15 as well as the concentration of Ara-C (Ara-C) and the metabolite Ara-U (Ara-U) as a function of time following injection of 14C-Ara-C itself. Injection of Ara-C-elaidate gave rise to substantially increased and prolonged exposure of rat-liver to both Ara-C-elaidate and Ara-C. with no detection of Ara-U up to 24 hours. This was in strong contrast to the liver concentration of Ara-C after administration of Ara-C as such. Liver concentration of Ara-C diminished to non-detectable levels after 4 hours, with the metabolite Ara-U present at all timepoints.

FIG. 20

Plasma levels of Ara-Celaidate and the metabolites Ara-C and Ara-U following intravenous administration of $^{14}$C-Ara-C-elaidate is shown as a function of time as well plasma levels of Ara-C and the metabolite Ara-U following intravenous administration of $^{14}$C-Ara-C as a function of time. Ara-C-elaidate administration give rise to prolonged plasma level of Ara-C, with detectable levels up to 72 hours in plasma following administration compared to 24 hours following Ara-C administration. Metabolism of Ara-C to Ara-U is less extensive, and starts later in animals which have received Ara-C-elaidate.

FIG. 21

Tissue concentration of total radioactivity is plotted as a function of time following intravenous administration of either $^{14}$C-Ara-C-elaidate (P) or $^{14}$C-Ara-C. The tissues shown in the graph are liver, spleen, lung, bone and bone marrow. Concentration of radioactivity following injection of $^{14}$C-Ara-C-elaidate is higher at all timepoints up to 120 hours for all the corresponding tissues.

The Ara-C esters of the present invention may be formulated with conventional carriers and excipients for administration.

As the most promising regime for the treatment of gliomas and other solid brain tumours, we currenty envisage local deposition of the active compounds at the site of the tumour to be attacked. For this purpose, the active compounds may preferably be presented as a lecithin micellar formulation. For example, the preferred treatment of brain metastasis will be by administration of a formulation of the Ara-C ester into the spinal fluid or into the tumour area by means of a dosing pump or similar device.

The Ara-C esters of the present invention may also be administrated systemically, either enterally or parenterally.

For enteral administration, the active compounds of the present invention may be presented as, e.g. soft or hard gelatine capsules, tablets, granules, grains or powders, drags, syrups, suspensions or solutions.

When administrated parenterally, preparations of Ara-C esters as injection or infusion solutions, suspensions or emulsions are suitable.

The preparation can contain inert or pharmacodynamically active additives, as well known to those skilled in the formulation arts. For instance, tablets or granulates can contain a series of binding agents, filler materials, emulsifying agents, carrier substances or dilutes. Liquid preparations may be present, for example, in the form of a sterile solution. Capsules can contain a filler material or thickening agent i addition to the active ingredient. Furthermore, flavour-improving additives as well as the substances usually used as preserving, stabilising, moisture-retaining and emulsifying agents, salts for varying the osmotic pressure, buffers and other additives may also be present.

The dosage in which the preparations according to this invention are administered will vary according to the mode of use and route of use, as well as to the requirements of the patient. In general a daily dosage for a systemic therapy for an adult average patient will be about 0.1–150 mg/kg body weight/day, preferably 1–50 mg/kg/day. For topical administration, an ointment, for instance, can contain from 0.1–10% by weight of the pharmaceutical formulation. especially 0.5–5% by weight.

I desired the pharmaceutical preparation containing the Ara-C esters can contain an antioxidant, e.g. tocopherol, N-methyl-tocopheramine, butylated hydroxyanisole, ascorbic acid or butylated hydroxytoluene.

Combination therapies, i.e. in which the administration of an Ara-C ester of this invention is carried out in conjunction with other therapies, e.g. surgery, radiation treatment and chemotherapy, are also contemplated. For example, the preferred treatment of brain tumours seems likely to be a combination of surgery and treatment with an Ara-C ester of this invention by systemic or local administration.

The esters of Ara-C used according to the invention may generally be prepared according to the following reaction equation:

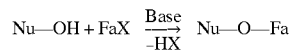

wherein Nu-OH stands for Ara-C. O is oxygen at 3' and for 5' position of the sugar moiety of Ara-C, Fa is an acyl group of a saturated or monounsaturated $C_{18}$ or $C_{20}$ fatty acid, and X may be Cl, Br or OR' wherein R' is Fa, $COCH_3$, COEt or $COCF_3$.

Thus, the reaction proceeds by acylation of the nucdeoside. This is accomplished by the use of suitable reactive derivatives of fatty acids, especially acid halides or acid anhydrides. When an acid halide such as an acid chloride is used, a tertiary amine catalyst, such as triethylamine, N,N-dimethylaniline, pyridine or N,N-dimethylaminopyridine is added to the reaction mixture to bind the liberated hydrohalic acid. The reactions are preferably carried out in an unreactive solvent such as N,N-dimethylformamide or a halogenated hydrocarbon, such as dichloromethane. If desired any of the above mentioned tertiary amine catalysts may be used as solvent, taking care that a suitable excess is present The reaction should preferably be kept between 5° C. and 250° C. After a period of 24 to 60 hours, the reaction will be essentially completed. The progress of the reaction can be followed using thin layer chromatography (TLC) and appropriate solvent systems. When the reaction is completed as determined by TLC, the product is extracted with an organic solvent and purified by chromatography and/or recrystallization from an appropriate solvent system. As more than one hydroxyl group and also an amino group are present in Ara-C, a mixture of acylated compounds will be produced. The individual mono- and di-O-esters required may be separated by, for instance, chromatography, crystallisation, supercritical extraction etc.

When it is desired to prepare a diester compound of formula I, in which $R_1$ and $R_2$ are the same acyl group, it is preferred to employ the above method using the appropriate acyl chloride in excess.

In order to prepare a diester compound of formula I, in which $R_1$ and $R_2$ are different, it is preferred to first prepare either the 3'- or 5'-monoester and then react the monoester with the proper acyl chloride.

This will be exemplified by the following working examples.

EXAMPLE 1

5'-O-(Elaidoyl) 1-β-D-arabinofuranosylcytosine$^{1,2}$

To a suspension of Ara-C HCl (1.007 g, 3.6×10$^{-3}$ mol) in 15 ml dimethylacetamide (DMA) was added a solution of Elaidoyl chloride (1.26 g, 4.2×10$^{-3}$ mol) in 5 ml DMA, and the mixture was stirred at 30° C. for 22 h. The solvent was evaporated at high vacuum and the residue was treated with hot ethyl acetate and filtered. The crude product was treated with 2 M NaHCO$_3$ aq., filtered off and purified on a column of silica gel with methanol (5 30%) in chloroform as the eluent system. Homogenous fractions were recrystallized to give 1.31 g (72%) of the title compound as a white solid (mp. 133–134° C.).

$^1$H NMR (DMSO-d$_6$, 300 MHz) δ: 7.58(1H, d, H-6), 7.18(2H, br.d, NH$_2$), 6.20(1H, d, H-5), 5.77(1H, d, H-1'), 5.65(2H, m, OH-2' and OH-3'), 5.47(2H, m, CH=CH), 4.43(1H, m, H-5'$_1$), 4.30(1H, m, H-5'$_2$), 4.1–4.0(3H, m, H-2', H-3' and H4'), 2.45(2H, t, CH$_2$—COO), 2.05(4H, m, CH$_2$—C=), 1.63(2H, m, CH$_2$—C—COO), 1.35(20H, m, CH$_2$), 0.97(3H, t, CH$_3$).

$^{13}$C NMR (DMSO-d$_6$, 75 MHz) δ: 172.8(COO), 165.59 (C4-N), 155.05(C=O 2), 142.86(C-6), 130.11(CH=CH), 92.54(C-5), 86.23(C-1'), 81,86(C-4'), 76.83(C-3'), 74.35(C-2'), 63.77(C-5'), 33.46, 31.95, 31.30, 29.03, 28.97, 28.85, 28.73, 28.52.28.43, 28.36, 24.48 and 22($CH_2$), 13.97($CH_3$).

EXAMPLE 2
3'-O(Elaidoyl) 1-β-D-arabinofuranosyl-cytosine[2,3]

A mixture of 2-hydroxyisobutyric acid (1.15 g, 12×$10^{-3}$ mol) and elaidoyl chloride (3. 1 g, 10×$10^{-3}$ mol) was stirred at 50° C. for 1 h. Thionyl chloride (1.5 ml, 21×$10^{-3}$ mol was added and stirring was continued for 2 h. The reaction mixture was kept by 50° C. at reduced pressure (40 mmHg) for 14 h. The formed 2-elaidoyloxy-2-methylpropanoyl chloride was used without any further purification, and suspended in 13 ml anhydrous acetonitrile. Cytidine (0.608 g, 2.5×$10^{-3}$ mol) was added, and the reaction mixture was stirred at 60° C. for 24 h. The solvent was evaporated off, and the residue treated with ether. The crude product was stirred in 40 ml pyridine-methanol 1:1 at 80° C. for 20 h, whereafter it was evaporated to dryness and the product purified on a column of silica gel. Homogenous fractions were recrystallized to give 0.446 g (35%) of the title compound as a white solid (mp. 164–166° C.).

$^1$H NMR (DMSO-$d_6$, 300 MHz) δ: 7.71 (1H, d, H-6), 7.2(2H, br.d, $NH_2$), 6.1(1H, d, H-5), 5.88(1H, d, H-1'), 5.81(1H, d, OH-2'), 5.45(2H, m, CH=CH), 5.18(1H, m, OH-5'), 5.06(1H, dd, H-3'), 4.18(1H, m, H-2'), 4.01(1H, m, H-4'), 3.75(2H, m, H-5'), 2.47(2H, t, $CH_2$—COO), 2.06(4H, m, $CH_2$—C=), 1.65(2H, m, $CH_2$—C—COO), 1.35(20H, m, $CH_2$), 0.97(3H, t, $CH_3$).

$^{13}$C NMR (DMSO-$d_6$, 75 MHz) δ: 172.15(COO), 165.67 (C4-N), 154.95(C=O), 142.72(C-6), 130.11 and 130.08 (CH=CH), 92.59(C-5), 86.24(C-1'), 82.75(C-4'), 78.72(C-3'), 72.29(C-2'), 61.15(C-5'), 33.43, 31.97, 31.30, 29.03, 28.99, 28.85, 28.73, 28.53, 28.41, 28.36, 24.40, 22.12($CH_2$), 13.97($CH_3$).

EXAMPLE 3
5'-O-(cis-11-eicosenoyl) 1-β-D-arabinofuranosyl-cytosine

To a suspension of Ara-C-HCl (0.87 g, 3.1×$10^{-3}$ mol) in 30 ml N,N-dimethylformamide was added a solution of cis-11-elcosenoyl chloride (1.06 g, 3.22×$10^{-3}$ mol) in 30 ml DMA, and the reaction mixture was stirred at 25° C. for 24 h. The solvents was evaporated at high vacuum and the residue was dissolved in 60 ml boiling ethanol to which was added 20 ml water and 20 ml saturated $NaHCO_3$ solution. The crude product was filtered off at room temperature and dissolved in 100 ml boiling ethanol (60% in water). The crude product was recrystallized from ethylacetate to give 1.1 g (66%) of the title compound as a white solid.

$^1$H NMR (DMSO-$d_6$, 300 MHz) δ: 7.45(1H, d, H-6), 7.1(2H, br.d, $NH_2$), 6.08(1H, d, H-1'), 5.65(1H, d, H-5), 5.55(2H, m, OH-2' and OH-3'), 5.32(2H, m, OH=CH), 4.25(1H, m, H-5'), 4.15(1H, m, H-5'), 4.0–3.85(3H, m, H-2', H-3', H-4'), 2.33(2H, t, $CH_2$—COO), 1.95(4H, m, $CH_2$—C=), 1.5(2H, m, $CH_2$—C—COO), 1.25(24H, m, $CH_2$), 0.85(3H, t, $CH_3$).

$^{13}$C NMR (DMSO-$d_6$, 75 MHz) δ: 172.79(COO), 165.59 (C-4), 155.08(C=O 2), 142.78(C6), 129.60(CH=CH), 92.52(C-5), 86.21(C;1'), 81.82(C4'), 76.75(C-3'), 74.25(C-2'), 63.76(C-5'), 33.41, 31.30, 29.11, 28.85, 28.72, 28.60, 28.42, 26.57, 24.46, 22.11 ($CH_2$), 13.94($CH_3$).

Ref.:
1. D. T. Gish et al.; J. Med. Chem. 14 (1971) 1159
2. E. K. Hamamura et al., J. Med. Chem. 19 (1976) 667
3. E. K. Hamamura et al, J. Med. Chem. 19 (1976) 654

What is claimed is:

1. An Ara-C derivative of formula (I):

(I)

wherein R is selected from the group consisting of elaidoyl, cis-eicosenoyl and trans-eicosenoyl.

2. A pharmaceutical composition, comprising an Ara-C derivative of formula (I), as defined in claim 1, and a pharmaceutically acceptable carrier or excipient therefor.

3. An Ara-C derivative of formula (I):

(I)

wherein R is eicosanoyl.

4. A pharmaceutical composition, comprising an Ara-C derivative of formula (I), as defined in claim 3, and a pharmaceutically acceptable carrier or excipient therefor.

5. 5'-elaidoyl-Ara-C.

6. A pharmaceutical composition, comprising 5'-elaidoyl-Ara-C and a pharmaceutically acceptable carrier or excipient therefor.

7. 5'-cis-eicosenoyl-Ara-C.

8. A pharmaceutical composition, comprising 5'-cis-eicosenoyl-Ara-C and a pharmaceutically acceptable carrier or excipient therefor.

9. 5'-trans-eicosenoyl-Ara-C.

10. A pharmaceutical composition, comprising 5'-trans-eicosenoyl-Ara-C and a pharmaceutically acceptable carrier or excipient therefor.

* * * * *

UNITED STATES PATENT AND TRADEMARK OFFICE
CERTIFICATE OF CORRECTION

PATENT NO.   : 6,335,322 B1
DATED        : January 1, 2002
INVENTOR(S)  : Finn Myhren et al.

It is certified that error appears in the above-identified patent and that said Letters Patent is hereby corrected as shown below:

Title page,
Item [56], OTHER PUBLICATIONS, after "R.L. Merriman, et al.: "Ling" should read
-- Lung --;
"W. Plnkett, et al." should read -- W. Plunkett, et al. -- and "Characteristic" should read
-- Characteristics --;
After R.Ohno, et al.: "arabimofuranosylcytosine" should read
-- arabinofuranosylcytosine --;
After R.A. Schwendener, et al.: "Carries" (both occurrences) should read -- Carriers --;
and
After "D.T. Warner, et al.: "arabinofuranosylctosine" should read
-- arabinofuranosylcytosine --.

Column 1,
Line 5, "May 28, 1998" should read -- July 12, 1996 --.

Column 2,
Line 31, "Arab" should read -- Ara-C --.

Column 3,
Line 65, "were" should read -- where --;
Line 67, "continius" should read -- continuous --.

Column 4,
Line 3, "equimolare" should read -- equimolar --;
Line 17, "072-R" should read -- 0- 72L --;
Line 25, "dinic" should read -- clinic --;
Line 29, "leukaemia's" should read -- leukaemias --;
Line 47, "paliativel" should read -- palliativel --; and
Line 64, "leukaemia's" should read -- leukaemias --.

Column 5,
Line 4, "non resistant" should read -- non-resistant --;
Line 6, "drug-eflux" should read -- drug-efflux --;
Line 7, "multi drug" should read -- multi-drug --;
Line 16, "chloroethyl)N" should read -- chloroethyl)-N --;
Line 31, "selected the" should read -- selected.  The --; and
Line 45, "nothing" should read -- noting --.

UNITED STATES PATENT AND TRADEMARK OFFICE
CERTIFICATE OF CORRECTION

PATENT NO. : 6,335,322 B1
DATED : January 1, 2002
INVENTOR(S) : Finn Myhren et al.

It is certified that error appears in the above-identified patent and that said Letters Patent is hereby corrected as shown below:

Column 6,
Line 54, "Raii" should read -- Raji --; and "Leptomeninpal" should read
-- Leptomengal --;
Line 57, "Bcell" should read -- B-cell --;
Line 59, "cistema" should read -- cisterna --; and
Line 62, "cistema" should read -- cisterna --.

Column 7,
Line 6, "symptom free" should read -- symptom-free --;
Line 18, "cistema" should read -- cisterna --;
Line 23, "experiment 3" should read -- experiment. 3 --;
Line 25, "promising 5/6" should read -- promising. 5/6 --;
Line 35, "cistema" should read -- cisterna --;
Line 38, "cistema" should read -- cisterna --;
Line 42, "equimotar" should read -- equimolar --;
Line 48, "cistema" should read -- cisterna --;
Line 54, "Raii" should read -- Raji --;
Line 58, "200 mglkg/day" should read -- 200 mg/kg/day --; and
Line 64, "Raii" should read -- Raji --.

Column 8,
Line 34, "Ara-Celaidate." should read -- Ara-C-elaidate. --;
Line 41, "$1 \times 10^5$," should read -- $1 \times 10^5$ --; and
Line 50, "Araelaidate" should read -- Ara-C-elaidate --.

Column 9,
Line 27, "$^{14}$C-" should read -- $^{14}$C- --;

Column 10,
Line 47, "$^{14}$C-Ara-C" should read -- $^{14}$C-Ara-C --;
Line 57, "Ara-Celaidate," should read -- Ara-C-elaidate --; and
Line 62, "give" should read -- gave --.

Column 11,
Line 39, "i" should read -- in --; and
Line 53, "I" should read -- If --.

UNITED STATES PATENT AND TRADEMARK OFFICE
CERTIFICATE OF CORRECTION

PATENT NO. : 6,335,322 B1
DATED : January 1, 2002
INVENTOR(S) : Finn Myhren et al.

It is certified that error appears in the above-identified patent and that said Letters Patent is hereby corrected as shown below:

Column 12,
Line 5, "and for" should read -- and/or --;
Line 10, "nucdeo" should read -- nucleo --;
Line 22, "present The" should read -- present.  The --; and
Line 23, "250º C." should read -- 25º C. --.

Column 13,
Line 3, "22($CH_2$)," should read -- 22.12($CH_2$), --;
Line 51, "OH=CH)," should read -- CH=CH), --; and
Line 52, "H-5')," second occurrence should read -- H-5'$_2$), --.

Signed and Sealed this

Ninth Day of July, 2002

Attest:

JAMES E. ROGAN
*Attesting Officer*    *Director of the United States Patent and Trademark Office*